US009557325B2

(12) United States Patent
McIntyre

(10) Patent No.: US 9,557,325 B2
(45) Date of Patent: *Jan. 31, 2017

(54) METHOD OF ALTERING THE BINDING SPECIFICITY OF PROTEINS BY OXIDATION-REDUCTION REACTIONS

(75) Inventor: John A. McIntyre, Indianapolis, IN (US)

(73) Assignee: REDOX-REACTIVE REAGENTS LLC, Beach Grove, IN (US)

( * ) Notice: Subject to any disclaimer, the term of this patent is extended or adjusted under 35 U.S.C. 154(b) by 609 days.

This patent is subject to a terminal disclaimer.

(21) Appl. No.: 11/108,826

(22) Filed: Apr. 19, 2005

(65) Prior Publication Data

US 2005/0260681 A1 Nov. 24, 2005

Related U.S. Application Data

(63) Continuation-in-part of application No. 10/863,365, filed on Jun. 9, 2004, now Pat. No. 7,368,542.

(60) Provisional application No. 60/476,607, filed on Jun. 9, 2003.

(51) Int. Cl.
| | |
|---|---|
| *G01N 33/564* | (2006.01) |
| *G01N 33/53* | (2006.01) |
| *C07K 16/00* | (2006.01) |
| *C07K 16/18* | (2006.01) |
| *G01N 33/537* | (2006.01) |
| *G01N 33/68* | (2006.01) |

(52) U.S. Cl.
CPC ........... *G01N 33/5306* (2013.01); *C07K 16/00* (2013.01); *C07K 16/18* (2013.01); *G01N 33/5375* (2013.01); *G01N 33/564* (2013.01); *G01N 33/6854* (2013.01); *C07K 2317/21* (2013.01)

(58) Field of Classification Search
USPC ............. 530/390.1, 390.5; 424/176.1, 177.1
See application file for complete search history.

(56) References Cited

U.S. PATENT DOCUMENTS

| | | | |
|---|---|---|---|
| 4,703,001 | A | 10/1987 | Vodian et al. |
| 4,950,612 | A | 8/1990 | Khanna et al. |
| 5,061,790 | A | 10/1991 | Elting |
| 5,939,394 | A | 8/1999 | Fleming et al. |
| 5,980,954 | A | 11/1999 | Bolton |
| 6,660,267 | B1 | 12/2003 | Carroll |
| 6,932,969 | B1 | 8/2005 | Bourel et al. |
| 7,195,881 | B2 | 3/2007 | Geffard |
| 2004/0082015 | A1 | 4/2004 | Geffard |
| 2005/0101016 | A1 | 5/2005 | McIntyre |

FOREIGN PATENT DOCUMENTS

| | | |
|---|---|---|
| CA | 2524325 | 3/2005 |
| EP | 0 778 025 | 6/1997 |
| WO | WO 89 05975 | 6/1989 |
| WO | WO 98/07436 | 2/1998 |
| WO | WO 00/74717 A1 | 12/2000 |
| WO | WO 2004/111608 | 12/2004 |

OTHER PUBLICATIONS

Conn et al, Outlines of Biochemistry, Fourth Edition, John Wiley & Sons, Inc., 1976, p. 23.*
John McIntyre, The Appearance and Disappearance of Antiphospholipid Autoantibodies Subsequent to Oxidation-Reduction Reactions, Thrombosis Research 2004, 114, pp. 579-587.
www.ucsfhealth.org/childrens/edu/bottleWeaning.html , provided by UCSF Children's Hospital, Patient Education, Baby Bottle Weaning, 2002-2007.
Ischiropoulus, Harry et al, "Oxidative Stress and Nitration in Neurodegeneration: Cause, effect, or association?", *J. Clin. Invest.* 2003 111:pp. 163-169.
Smith, Mark A., et al, "Widespread Peroxynitrite-Mediated Damage in Alzheimer's Disease", *J. Neuroscience*, Apr. 15, 1997, 17(8) pp. 2653-2657.
McIntyre, John A., "The Appearance and Disappearance of Antiphospholipid Autoantibodies Subsequent to Oxidation-reduction Reactions", *Thrombosis Research* 2004, 114, pp. 579-587.
McIntyre, John A., et al, "Autoantibodies Unmasked by Redox Recations", *J. Autoimmun* 2005; 24 pp. 311-317.
McIntyre, John A., et al "Redox-reactive Autoantibodies: Detection and Physiological Relevance", *Autoimmunity Reviews* 2006; 5 pp. 76-83.
Sokol, D.K. et al, "Testing for Antiphospholipid Antibody (aPL) Specificities in Retrospective 'Normal' Cerebral Spinal Fluid (CSF)", *Clin Develop. Immunol.* 2005; 11: pp. 7-12.
Adams, J. Paige et al, "Molecular Psychology: Roles for the ERK MAP Kinase Cascade in Memory", *Annu. Rev. Pharmacol. Toxicol.* 2002 42 pp. 135-163.
Hindley, Alison et al, "Extracellular Signal Regulated Kinase (ERK)/mitogen Activated Protein Kinase (MAPK)-independent Functions of Rat Kinases", *J. Cell Science*, 2002; 115, pp. 1575-1581.
Cheung et al, "Emerging Role for ERK as a Key Regulator of Neuronal Apoptosis", *Science*, 2004; 251: pp. 1-3.
Chapman, J. et al, "Antiphospholipid Antibodies Permeablizie and Depolarize Brain Synaptoneurosomes", *Lupus* 1999; 8: pp. 127-133.
D'Aandrea, PhD, Michael R., "Evidence that Immunoglobulin-positive Neurons in Alzheimer's Disease are Dying Via the Classical Antibody-dependent Complement Pathway", *Am. J. Alzheimer's Dis. Other Dimentas* 2005; 20; pp. 144-150.
Colucci-D'Amato, L. et al, "Chronic Activation of ERK and Neurodegenerative Diseases", *Bioassays*, 2003: 25, pp. 1085-1095.
Robertson and Greaves, Blood Rev 20: 2006, pp. 201-212.
Gallo et al., J. Neurol Sc. 122, 1994, pp. 97-101.

(Continued)

*Primary Examiner* — Yunsoo Kim
(74) *Attorney, Agent, or Firm* — Fitch, Even, Tabin & Flannery, LLP

(57) ABSTRACT

The binding specificity of at least one protein suspended or dissolved in a liquid medium is reversibly altered by exposing the protein to an oxidizing agent or an electric current. A masked protein such as an autoantibody can be detected, isolated and recovered from a biological fluid by subjecting the biological fluid to an oxidizing agent or an electric current to change the binding specificity of masked proteins contained therein.

45 Claims, 34 Drawing Sheets

(56) References Cited

OTHER PUBLICATIONS

Tanne et al., Curr Rheumat Rep 3, 2001, 286-292.
Jedryka-Goral. Et al. Clin Rheumatol 19, 2000, pp. 306-310.
Mosek et al. Dem. Ger Cog. Disorder 11:, 2000, pp. 36-38.
Oomen et al. Psychiat Res 58, 83-88, 1995.
Gomez-Puerta et al., Rheumatol 44:, 2005, pp. 95-99.
Sokol et al., Neurology 55: 2000, pp. 1379-1381.
Martinez-Cordero et al., J. Invest Allerg Clin Immunol 7, 1997, pp. 596-601.
International Preliminary Report on Patentability dated Aug. 22, 2008, for PCT/US07/01582.
Australian Search Report dated Jun. 17, 2008, on pat. applic. No. 2004248155.
J. Cabiedes et al., Hidden Anti-Phospholipid Antibodies in Normal Human Sera Circulate as Immune Complexes Whose Antigen can be Removed by Heat, Acid, Hypermolar Buffers or Phospholipase Treatments, Eur. J. Immunol. pp. 2108-2114.
Office Action of Japanese Patent Application No. 515229/2006 dated Dec. 16, 2008.
Office Action of Patent Office of the People's Republic of China Application No. 200480015987.9 dated Feb. 6, 2009.
EP Office Action App. No. 04 754 487.9 dated Mar. 5, 2009.
International Preliminary Report on Patentability, PCT/US2006/12802, Jan. 7, 2008.
Leroy E. Hood et al., *Immunology* 2$^{nd}$ Edition, Chapter 9: Immune Effector Mechanisms and the Complement System, Benjamin/Cummings Publishing Company, Inc., 1984.
McIntyre, et al., Redox-reactive antiphospholipid antibody differences between serum from Alzheimer's patients and age-matched controls, Autoimmunity, First published on Aug. 3, 2009.
Nagababu, et al., Formation of Fluorescent Heme Degradation Products during the Oxidation of Hemoglobin by Hydrogen Peroxide, Biochemical and Biophysical Research Communications, 247, 1998, pp. 592-596.
Teunissen, et al., Biochemical markers related to alzheimer's dementia in serum and cerebrospinal fluid, Neurobiology of Aging, 23, 2002, pp. 485-508.
Canadian Office Action, CA Application No. 2,602,635, Sep. 9, 2009.
Pauling, Linus, General Chemistry: An Introduction to Descriptive Chemistry and Modern Chemical Theory, 2$^{nd}$ Edition, W.H. Freeman and Company, p. 523.
Indian Office Action, in Application No. 4760/CHENP/2007, undated but faxed Sep. 10, 2008.
Australian Examiner's first report on patent application No. 2007225434, Aug. 24, 2009.
EPO Communication pursuant to Article 94(3) EPC, European Application No. 07 749 017.5, Jan. 5, 2010.
Supplementary Partial European Search Report, EP Application No. 04 75 4487, Jun. 19, 2006.
EPO Communication pursuant to Article 94(3) EPC, EP Application No. 04 754 487.9, Jul. 24, 2007.
EPO Communication pursuant to Article 94(3) EPC, EP Application No. 04 754 487.9, Apr. 9, 2008.
EPO Communication pursuant to Article 94(3) EPC, EP Application No. 04 754 487.9, Aug. 14, 2009.
EPO Communication pursuant to Article 94(3) EPC, EP Application No. 04 754 487.9, May 7, 2010.
Supplementary European Search Report, EP Application No. 07 749 017.5, Dec. 3, 2009.
Canadian Office Action, Canadian Patent Application No. 2,602,635, Canadian Intellectual Property Office, Feb. 25, 2011.
Lacroix-Desmazes, et al., "Autoantibodies to factor VIII", Autoimmunity Reviews 1 (2002), pp. 105-110.
Ruffatti, et al., "Nuclear Membrane-Staining Antinuclear Antibody in Patients with Primary Biliary Cirrhosis", Journal of Clinical Immunology, vol. 5, No. 5, 1985.
Borg, et al., "protein tyrosine phosphatase-like protein IA2-antibodies plus glutamic acid decarboxylase 65 Antibodies (GADA) indicates autoimmunity as frequently as islet cell antibodies assay in children with recently diagnosed diabetes mellitus", Clinical Chemistry, vol. 43, No. 12, pp. 2358-2363, (1997).
Honnorat, et al., "Cellular Ataxia with Anti-Glutamic Acid Decarboxylase Antibodies", Archives or Neurology, vol. 48, No. 2, Feb. 2011, pp. 225-230.
Canadian Office Action dated Feb. 24, 2015 in Canadian Patent Application No. 2,524,325.
Jean-Luc Senecal and Yves Raymond, "Autoantibodies to Major and Minor Nuclear Lamins Are Not Restricted to Autoimmune Diseases", Clin Immunol Immunopathol., May 1992, 63(2):115-25.
M. Galli, et al., "Effect of Antiphospholipid Antibodies on Procoagulant Activity of Activated Platelets and Platelet-derived Microvesicles", BR J Haematol, Mar. 1993; 83(3):466-72.
Dawn Wagenknecht, et al., "The Evolution, Evaluation and Interpretation of Antiphospholipid Antibody Assays", Clinical Immunology Newsletter, 1995, vol. 15, No. 2/3 pp. 28-38.

* cited by examiner

In-house aPL ELISA*

| PS | CL | PE | PC |
|---|---|---|---|
| IgG | IgG | IgG | IgG |
| IgA | IgA | IgA | IgA |
| IgM | IgM | IgM | IgM |

\* In the presence (dependent) and absence (independent) of phospholipid-binding plasma proteins

Figure 1

Unconditioned broth + blood

Antiphospholipid Antibody (aPL) Results

|  |  | PL binding protein | | Normal ranges |
|---|---|---|---|---|
|  |  | dependent | independent |  |
| aPS | IgG | 24 MoM +++ | 3 MoM | ≤ 4 MoM |
|  | IgA | 8 MoM + | 2 MoM | ≤ 3 MoM |
|  | IgM | 8 MoM + | 1 MoM | ≤ 5 MoM |
| aCL | IgG | 12 MoM +++ | 2 MoM | ≤ 4 MoM |
|  | IgA | 12 MoM +++ | 2 MoM | ≤ 4 MoM |
|  | IgM | 16 MoM +++ | 1 MoM | ≤ 6 MoM |
| aPE | IgG | 36 MoM +++ | 7 MoM + | ≤ 4 MoM |
|  | IgA | 7 MoM + | 2 MoM | ≤ 3 MoM |
|  | IgM | 8 MoM + | 3 MoM | ≤ 5 MoM |
| aPC | IgG | 2 MoM | 4 MoM | ≤ 4 MoM |
|  | IgA | 1 MoM | 3 MoM | ≤ 3 MoM |
|  | IgM | 6 MoM + | 5 MoM + | ≤ 4 MoM |

Figure 2 aPL range for 7 healthy persons

Antiphospholipid Antibody (aPL) Results

|  |  | PL binding protein | | Normal ranges |
|---|---|---|---|---|
|  |  | dependent | independent |  |
| aPS | IgG | 17 - 25 +++ | 5 - 14 ++ | ≤ 4 MoM |
|  | IgA | 4 - 14 ++ | 4 - 8 + | ≤ 3 MoM |
|  | IgM | 5 - 16 ++ | 3 - 13 ++ | ≤ 5 MoM |
| aCL | IgG | 7 - 10 ++ | 1 - 3 | ≤ 4 MoM |
|  | IgA | 6 - 19 ++ | 2 - 7 + | ≤ 4 MoM |
|  | IgM | 6 - 17 ++ | 2 - 13 ++ | ≤ 6 MoM |
| aPE | IgG | 22 - 33 +++ | 7 - 20 ++ | ≤ 4 MoM |
|  | IgA | 3 - 7 + | 1 - 5 + | ≤ 3 MoM |
|  | IgM | 2 - 7 + | 2 - 6 + | ≤ 5 MoM |
| aPC | IgG | 1 - 2 | 1 - 4 | ≤ 4 MoM |
|  | IgA | 1 - 4+ | 5 - 20 ++ | ≤ 3 MoM |
|  | IgM | 1 - 8 + | 4 - 17 ++ | ≤ 4 MoM |

Figure 3

Horse RBC, human serum, broth

Antiphospholipid Antibody (aPL) Results

|  |  | PL binding protein | | Normal ranges |
|---|---|---|---|---|
|  |  | dependent | independent |  |
| aPS | IgG | 14 MoM +++ | 1 MoM | ≤ 4 MoM |
|  | IgA | 5 MoM + | 1 MoM | ≤ 3 MoM |
|  | IgM | 19 MoM +++ | 1 MoM | ≤ 5 MoM |
| aCL | IgG | 2 MoM | 1 MoM | ≤ 4 MoM |
|  | IgA | 13 MoM +++ | 1 MoM | ≤ 4 MoM |
|  | IgM | 27 MoM +++ | 1 MoM | ≤ 6 MoM |
| aPE | IgG | 1 MoM | 2 MoM | ≤ 4 MoM |
|  | IgA | 1 MoM | 1 MoM | ≤ 3 MoM |
|  | IgM | 1 MoM | 4 MoM | ≤ 5 MoM |
| aPC | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 4 MoM |

Figure 4

Human RBC, horse serum, broth

Antiphospholipid Antibody (aPL) Results

|  |  | PL binding protein | | Normal ranges |
|---|---|---|---|---|
|  |  | dependent | independent |  |
| aPS | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 5 MoM |
| aCL | IgG | 1 MoM | 1 MoM | ≤ 4 MoM |
|  | IgA | 1 MoM | 1 MoM | ≤ 4 MoM |
|  | IgM | 1 MoM | 1 MoM | ≤ 6 MoM |
| aPE | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 5 MoM |
| aPC | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 4 MoM |

Figure 5

Blood in rocking vial at 22° C

Antiphospholipid Antibody (aPL) Results

|  |  | PL binding protein | | Normal ranges |
|---|---|---|---|---|
|  |  | dependent | independent |  |
| aPS | IgG | 6 MoM + | 3 MoM | ≤ 4 MoM |
|  | IgA | 1 MoM | 1 MoM | ≤ 3 MoM |
|  | IgM | 1 MoM | 1 MoM | ≤ 5 MoM |
| aCL | IgG | 2 MoM | 2 MoM | ≤ 4 MoM |
|  | IgA | 1 MoM | 1 MoM | ≤ 4 MoM |
|  | IgM | 1 MoM | 1 MoM | ≤ 6 MoM |
| aPE | IgG | 4 MoM | 1 MoM | ≤ 4 MoM |
|  | IgA | 1 MoM | 1 MoM | ≤ 3 MoM |
|  | IgM | 1 MoM | 1 MoM | ≤ 5 MoM |
| aPC | IgG | 2 MoM | 2 MoM | ≤ 4 MoM |
|  | IgA | 1 MoM | 1 MoM | ≤ 3 MoM |
|  | IgM | 1 MoM | 6 MoM + | ≤ 4 MoM |

Figure 6

Replace charcoal: 0.7mm Degalan

Antiphospholipid Antibody (aPL) Results

|  |  | PL binding protein | | Normal ranges |
|---|---|---|---|---|
|  |  | dependent | independent |  |
| aPS | IgG | 31 MoM +++ | 3 MoM | ≤ 4 MoM |
|  | IgA | 3 MoM | 1 MoM | ≤ 3 MoM |
|  | IgM | 2 MoM | 1 MoM | ≤ 5 MoM |
| aCL | IgG | 7 MoM + | 2 MoM | ≤ 4 MoM |
|  | IgA | 5 MoM + | 2 MoM | ≤ 4 MoM |
|  | IgM | 10 MoM +++ | 1 MoM | ≤ 6 MoM |
| aPE | IgG | 8 MoM + | 1 MoM | ≤ 4 MoM |
|  | IgA | 2 MoM | 1 MoM | ≤ 3 MoM |
|  | IgM | 1 MoM | 1 MoM | ≤ 5 MoM |
| aPC | IgG | 2 MoM | 1 MoM | ≤ 4 MoM |
|  | IgA | 1 MoM | 1 MoM | ≤ 3 MoM |
|  | IgM | 1 MoM | 4 MoM | ≤ 4 MoM |

Figure 7

Blood in stationary vial at 37° C

Antiphospholipid Antibody (aPL) Results

|  |  | PL binding protein | | Normal ranges |
|---|---|---|---|---|
|  |  | dependent | independent |  |
| aPS | IgG | 1 MoM | 1 MoM | ≤ 4 MoM |
|  | IgA | 1 MoM | 1 MoM | ≤ 3 MoM |
|  | IgM | 2 MoM | 1 MoM | ≤ 5 MoM |
| aCL | IgG | 1 MoM | 1 MoM | ≤ 4 MoM |
|  | IgA | 1 MoM | 1 MoM | ≤ 4 MoM |
|  | IgM | 7 MoM + | 1 MoM | ≤ 6 MoM |
| aPE | IgG | 1 MoM | 1 MoM | ≤ 4 MoM |
|  | IgA | 1 MoM | 1 MoM | ≤ 3 MoM |
|  | IgM | 4 MoM | 3 MoM | ≤ 5 MoM |
| aPC | IgG | 1 MoM | 3 MoM | ≤ 4 MoM |
|  | IgA | 1 MoM | 1 MoM | ≤ 3 MoM |
|  | IgM | 3 MoM | 7 MoM + | ≤ 4 MoM |

Figure 8

Effect of heating at 56° C

Antiphospholipid Antibody (aPL) Results

|  |  | PL binding protein | | Normal ranges |
|---|---|---|---|---|
|  |  | preheat | heated |  |
| aPS | IgG | 47 MoM +++ | 69 MoM +++ | ≤ 4 MoM |
|  | IgA | 12 MoM +++ | 18 MoM +++ | ≤ 3 MoM |
|  | IgM | 3 MoM | 1 MoM | ≤ 5 MoM |
| aCL | IgG | 13 MoM +++ | 16 MoM +++ | ≤ 4 MoM |
|  | IgA | 16 MoM +++ | 22 MoM +++ | ≤ 4 MoM |
|  | IgM | 12 MoM +++ | 16 MoM +++ | ≤ 6 MoM |
| aPE | IgG | 48 MoM +++ | 44 MoM +++ | ≤ 4 MoM |
|  | IgA | 6 MoM + | 8 MoM + | ≤ 3 MoM |
|  | IgM | 2 MoM | 1 MoM | ≤ 5 MoM |
| aPC | IgG | 5 MoM + | 6 MoM + | ≤ 4 MoM |
|  | IgA | 1 MoM | 2 MoM | ≤ 3 MoM |
|  | IgM | 1 MoM | 3 MoM | ≤ 4 MoM |

Figure 9

Becton Dickinson* culture vial

Antiphospholipid Antibody (aPL) Results

|  |  | PL binding protein | | Normal ranges |
|---|---|---|---|---|
|  |  | dependent | independent |  |
| aPS | IgG | 11 MoM +++ | 3 MoM | ≤ 4 MoM |
|  | IgA | failure | failure | ≤ 3 MoM |
|  | IgM | 4 MoM | 1 MoM | ≤ 5 MoM |
| aCL | IgG | 6 MoM + | 4 MoM | ≤ 4 MoM |
|  | IgA | 5 MoM + | 5 MoM + | ≤ 4 MoM |
|  | IgM | 9 MoM + | 1 MoM | ≤ 6 MoM |
| aPE | IgG | 32 MoM +++ | 1 MoM | ≤ 4 MoM |
|  | IgA | 2 MoM | 1 MoM | ≤ 3 MoM |
|  | IgM | 10 MoM +++ | 1 MoM | ≤ 5 MoM |
| aPC | IgG | 1 MoM | 1 MoM | ≤ 4 MoM |
|  | IgA | 1 MoM | 1 MoM | ≤ 3 MoM |
|  | IgM | 1 MoM | 1 MoM | ≤ 4 MoM |

*Replacing Biomerieux

Figure 10

Anaerobic culture vial broth + blood

Antiphospholipid Antibody (aPL) Results

| | | PL binding protein | | Normal ranges |
|---|---|---|---|---|
| | | dependent | independent | |
| aPS | IgG | 16 MoM +++ | 10 MoM +++ | ≤ 4 MoM |
| | IgA | 3 MoM | 2 MoM | ≤ 3 MoM |
| | IgM | 9 MoM + | 5 MoM | ≤ 5 MoM |
| aCL | IgG | 8 MoM + | 3 MoM | ≤ 4 MoM |
| | IgA | 4 MoM | 1 MoM | ≤ 4 MoM |
| | IgM | 17 MoM +++ | 3 MoM | ≤ 5 MoM |
| aPE | IgG | 33 MoM +++ | 10 MoM +++ | ≤ 4 MoM |
| | IgA | 4 MoM + | 1 MoM | ≤ 3 MoM |
| | IgM | 9 MoM + | 3 MoM | ≤ 5 MoM |
| aPC | IgG | 1 MoM | 2 MoM | ≤ 4 MoM |
| | IgA | 1 MoM | 1 MoM | ≤ 3 MoM |
| | IgM | 3 MoM | 5 MoM + | ≤ 4 MoM |

Figure 11

Replace RBC with K562*

Antiphospholipid Antibody (aPL) Results

| | | PL binding protein | | Normal ranges |
|---|---|---|---|---|
| | | dependent | independent | |
| aPS | IgG | 10 MoM +++ | 6 MoM + | ≤ 4 MoM |
| | IgA | 5 MoM + | 1 MoM | ≤ 3 MoM |
| | IgM | 1 MoM | 1 MoM | ≤ 5 MoM |
| aCL | IgG | 3 MoM | 1 MoM | ≤ 4 MoM |
| | IgA | 7 MoM + | 1 MoM | ≤ 4 MoM |
| | IgM | 2 MoM | 1 MoM | ≤ 6 MoM |
| aPE | IgG | 14 MoM +++ | 4 MoM | ≤ 4 MoM |
| | IgA | 7 MoM + | 2 MoM | ≤ 3 MoM |
| | IgM | 1 MoM | 1 MoM | ≤ 5 MoM |
| aPC | IgG | 1 MoM | 2 MoM | ≤ 4 MoM |
| | IgA | 1 MoM | 3 MoM | ≤ 3 MoM |
| | IgM | 1 MoM | 3 MoM | ≤ 4 MoM |

Total cell count $11.3 \times 10^6$

Figure 12

Replace broth with RPMI and beads

Antiphospholipid Antibody (aPL) Results

| | | PL binding protein | | Normal ranges |
|---|---|---|---|---|
| | | dependent | independent | |
| aPS | IgG | 1 MoM | 1 MoM | ≤ 4 MoM |
| | IgA | 1 MoM | 1 MoM | ≤ 3 MoM |
| | IgM | 2 MoM | 2 MoM | ≤ 5 MoM |
| aCL | IgG | 1 MoM | 2 MoM | ≤ 4 MoM |
| | IgA | 1 MoM | 1 MoM | ≤ 4 MoM |
| | IgM | 2 MoM | 2 MoM | ≤ 6 MoM |
| aPE | IgG | 1 MoM | 1 MoM | ≤ 4 MoM |
| | IgA | 1 MoM | 1 MoM | ≤ 3 MoM |
| | IgM | 2 MoM | 4 MoM | ≤ 5 MoM |
| aPC | IgG | 1 MoM | 1 MoM | ≤ 4 MoM |
| | IgA | 1 MoM | 1 MoM | ≤ 3 MoM |
| | IgM | 3 MoM | 5 MoM + | ≤ 4 MoM |

Figure 13

Placental cord blood + broth

Antiphospholipid Antibody (aPL) Results

| | | PL binding protein | | Normal ranges |
|---|---|---|---|---|
| | | dependent | independent | |
| aPS | IgG | 42 MoM +++ | 27 MoM +++ | ≤ 4 MoM |
| | IgA | 1 MoM | 1 MoM | ≤ 3 MoM |
| | IgM | 1 MoM | 1 MoM | ≤ 5 MoM |
| aCL | IgG | 14 MoM +++ | 6 MoM + | ≤ 4 MoM |
| | IgA | 1 MoM | 1 MoM | ≤ 4 MoM |
| | IgM | 2 MoM | 1 MoM | ≤ 6 MoM |
| aPE | IgG | 38 MoM +++ | 23 MoM +++ | ≤ 4 MoM |
| | IgA | 1 MoM | 1 MoM | ≤ 3 MoM |
| | IgM | 1 MoM | 1 MoM | ≤ 5 MoM |
| aPC | IgG | 1 MoM | 6 MoM + | ≤ 4 MoM |
| | IgA | 1 MoM | 1 MoM | ≤ 3 MoM |
| | IgM | 1 MoM | 1 MoM | ≤ 4 MoM |

Figure 14

Replace RBC with sodium nitroprusside*

Antiphospholipid Antibody (aPL) Results

| | | PL binding protein | | Normal ranges |
|---|---|---|---|---|
| | | dependent | independent | |
| aPS | IgG | 18 MoM +++ | 5 MoM + | ≤ 4 MoM |
| | IgA | 8 MoM + | 4 MoM + | ≤ 3 MoM |
| | IgM | 1 MoM | 1 MoM | ≤ 5 MoM |
| aCL | IgG | 7 MoM + | 1 MoM | ≤ 4 MoM |
| | IgA | 7 MoM | 1 MoM | ≤ 4 MoM |
| | IgM | 1 MoM | 1 MoM | ≤ 6 MoM |
| aPE | IgG | 23 MoM +++ | 9 MoM + | ≤ 4 MoM |
| | IgA | 3 MoM | 4 MoM + | ≤ 3 MoM |
| | IgM | 1 MoM | 1 MoM | ≤ 5 MoM |
| aPC | IgG | 1 MoM | 2 MoM | ≤ 4 MoM |
| | IgA | 2 MoM | 1 MoM | ≤ 3 MoM |
| | IgM | 1 MoM | 1 MoM | ≤ 4 MoM |

Lupus anticoagulant activity
Whole blood broth

| | Immediate Mix 1:1 | Incubated Mix 1:1 1-2 hours |
|---|---|---|
| dRVVT | 46.7 sec* | 104.4 sec |
| dPT | 42.5 sec† | 48.7 sec |

* normal = 28 - 49 sec   † normal = 29.6 - 41.8

Figure 16

Histogram Statistics
Log Data Units: Channel Values
Patient ID: xxx  CELLS
Gate: G4                          (Pooled NHS)
Total Events: 10000

| % Total | Mean | Geo Mean | CV | Median |
|---|---|---|---|---|
| 3.78 | 748.20 | 744.62 | 9.60 | 743.50 |

Histogram Statistics
Log Data Units: Channel Values
Patient ID: xxx  CELLS  (Normal person's
Gate: G4                       serum)
Total Events: 10000

| % Total | Mean | Geo Mean | CV | Median |
|---|---|---|---|---|
| 4.13 | 732.09 | 726.99 | 10.96 | 737.00 |

Histogram Statistics
Log Data Units: Channel Values
Patient ID: xxxx  CELLS  (Normal person's
Gate: G4                serum treated by
Total Events: 10000     invention)

| % Total | Mean | Geo Mean | CV | Median |
|---|---|---|---|---|
| 4.72 | 872.61 | 866.72 | 11.38 | 864.00 |

Histogram Statistics
Log Data Units: Channel Values
Patient ID: xxxx  CELLS
Gate: G4
Total Events: 10000     (Positive control)

| % Total | Mean | Geo Mean | CV | Median |
|---|---|---|---|---|
| 5.16 | 834.75 | 833.53 | 5.54 | 827.50 |

ANA Antibodies Identified by ImmunoConcepts Laboratories*

Using the RELISA® screening assay†

| Sample | Units |
|---|---|
| Cord serum | 0 |
| Cord stationary | 27 |
| Cord shake | 75 |
| ACS serum | 0 |
| ACS shake + heat | 90 |

*Sacramento, California  † < 10 units = neg  10-15 units = borderline

Antiphospholipid Antibody (aPL) Results

| | | PL binding protein | | Normal ranges |
|---|---|---|---|---|
| | | dependent | independent | |
| aPS | IgG | 31 MoM +++ | 4 MoM | ≤ 4 MoM |
| | IgA | 1 MoM | 1 MoM | ≤ 3 MoM |
| | IgM | 1 MoM | 1 MoM | ≤ 5 MoM |
| aCL | IgG | 7 MoM + | 1 MoM | ≤ 4 MoM |
| | IgA | 1 MoM | 1 MoM | ≤ 4 MoM |
| | IgM | 1 MoM | 1 MoM | ≤ 6 MoM |
| aPE | IgG | 32 MoM +++ | 3 MoM | ≤ 4 MoM |
| | IgA | 1 MoM | 1 MoM | ≤ 3 MoM |
| | IgM | 1 MoM | 1 MoM | ≤ 5 MoM |
| aPC | IgG | 5 MoM + | 1 MoM | ≤ 4 MoM |
| | IgA | 1 MoM | 1 MoM | ≤ 3 MoM |
| | IgM | 1 MoM | 1 MoM | ≤ 4 MoM |

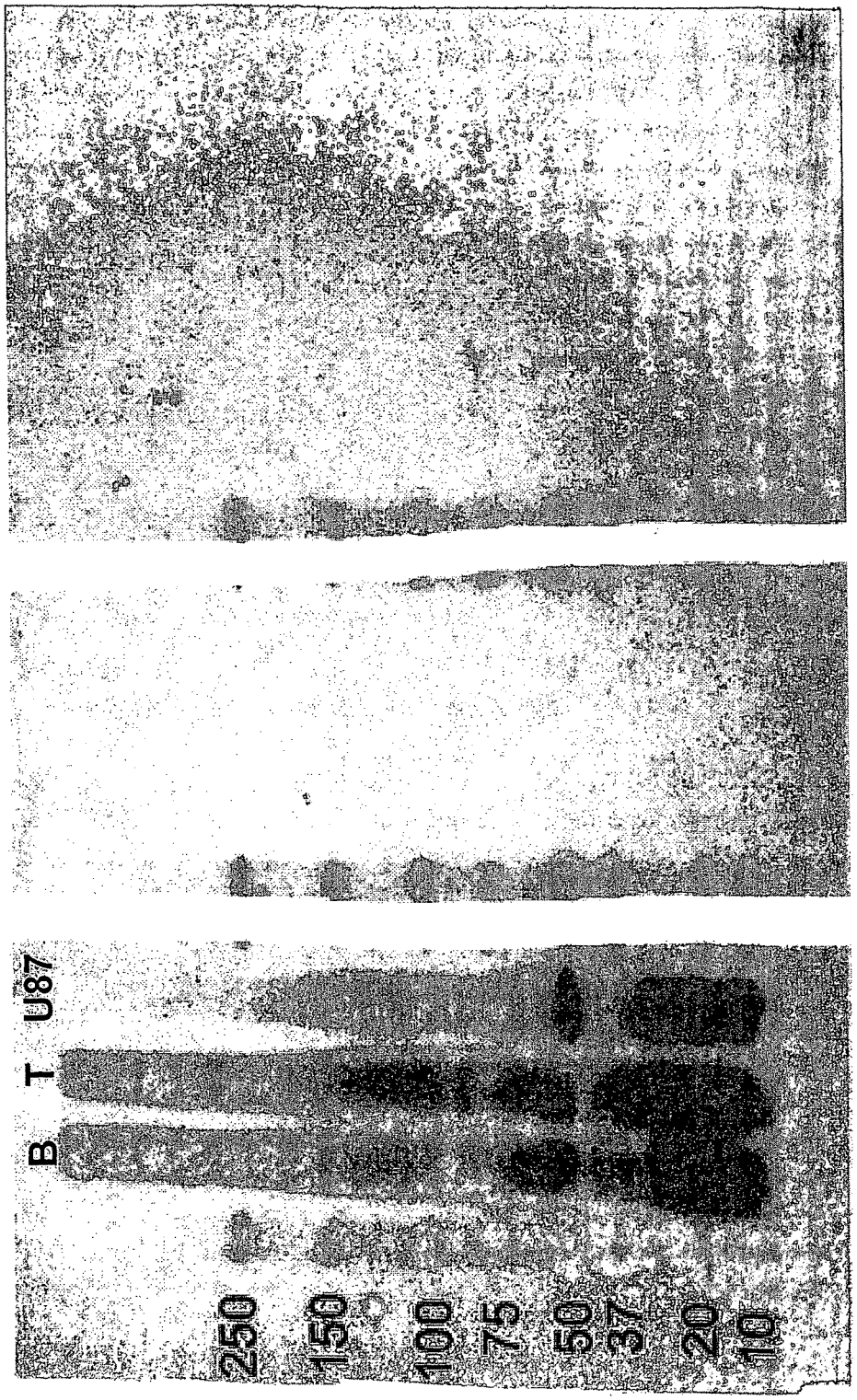

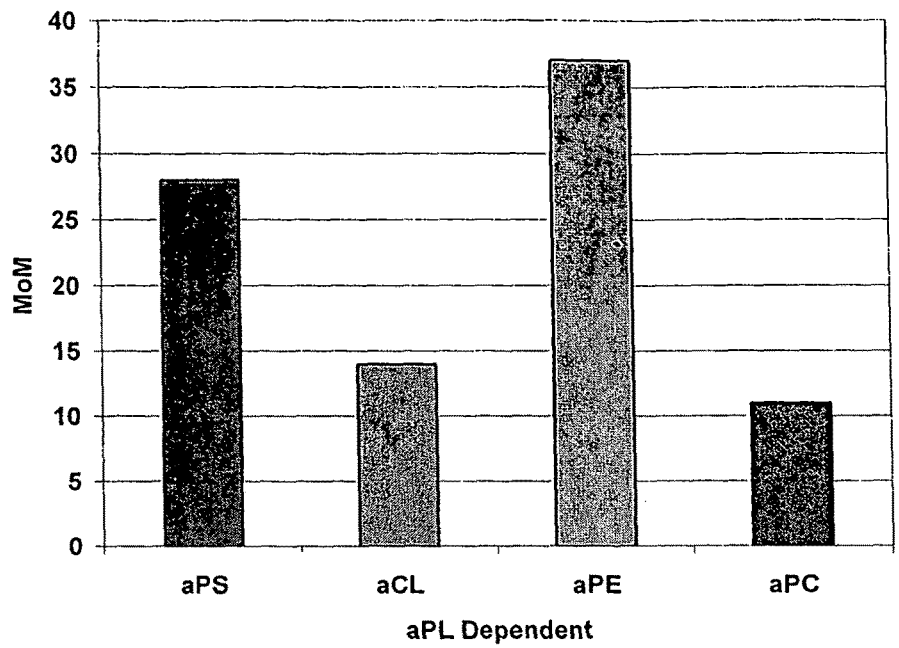
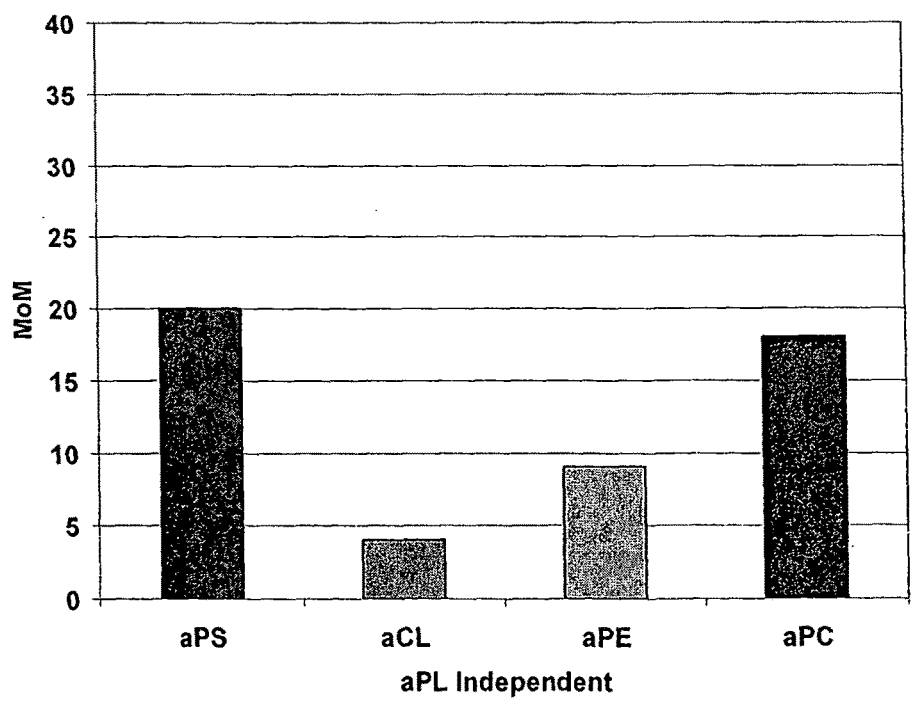

Figure 38A
Figure 38B
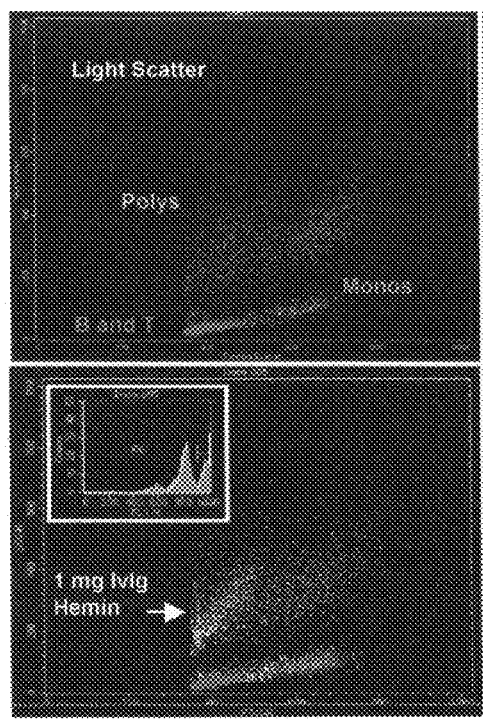
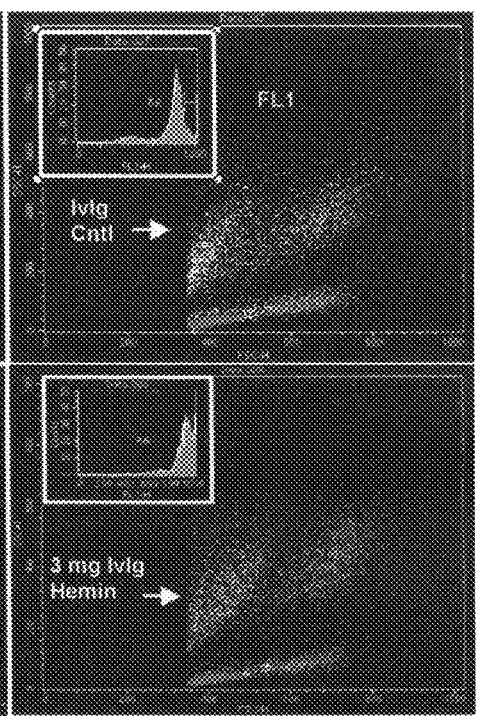
FIGURE 38C
FIGURE 38D

METHOD OF ALTERING THE BINDING SPECIFICITY OF PROTEINS BY OXIDATION-REDUCTION REACTIONS

The present application is a continuation-in-part of U.S. patent application Ser. No. 10/863,365, filed on Jun. 9, 2004, now U.S. Pat. No. 7,368,542, issued May 6, 2008, which application claimed the benefit of the filing date of U.S. Provisional Application No. 60/476,607, filed Jun. 9, 2003. These applications are incorporated herein by reference.

FIELD OF INVENTION

The present invention relates to a method of altering a binding specificity of a protein that has a binding specificity that can be altered by oxidation-reduction reactions. The present invention further relates to a method of reversibly altering the binding specificity of antibodies, particularly masked autoantibodies that are naturally present in the blood, plasma, serum or other bodily fluids of normal subjects.

BACKGROUND OF THE INVENTION

The term "autoimmune disease" refers to a group of diseases wherein the immune system mistakenly attacks cells, tissues and organs of a person's own body. Typically, autoimmune diseases involve antibody binding of the body's own components, such as common proteins and lipids. Antibodies that bind to self-compounds (or, more typically, to compounds that are so common that they are found in every organism) are referred to as autoantibodies. As an example, autoantibody binding of phospholipids and/or phospholipid-binding plasma proteins is associated with diseases such as systemic lupus erythematosus (SLE), deep vein and recurrent arterial thrombosis, pulmonary embolisms, recurrent spontaneous abortion, thrombocytopenia, chorea, epilepsy, livedo, idiopathic pulmonary hypertension, rheumatological conditions and a host of collagenous diseases. Other diseases associated with autoantibodies include multiple sclerosis, Crohn's disease, discoid lupus erythematosus, Hashimoto's thyroiditis, psoriasis, diabetes and rheumatoid arthritis. There are about 80 different autoimmune diseases, and as a group, these diseases affect millions of people.

A conventional theory regarding the etiology of autoimmune diseases has been that these diseases are caused by an overproduction of autoantibodies in the diseased individual, possibly due to an overexpression of a gene encoding such autoantibodies. According to this theory, the blood of an affected individual contains an elevated level of the particular autoantibody causing the disease, while the blood of a normal individual contains none of the autoantibody or only a trivial amount. This theory is seemingly supported by conventional assays, in which abundant autoantibodies can be detected in blood, or blood products such as plasma or serum, from subjects having an autoimmune disease, whereas only a zero or minimal amount of autoantibodies can be detected in blood or blood products from subjects that do not have an autoimmune disease.

The present invention is based on the remarkable discovery, reported herein, that blood from normal individuals in fact contains a significant number of autoantibodies, in a wide variety of types and specificities. It is possible to detect and isolate these autoantibodies from blood or a blood product of a normal individual if the blood or blood product is treated by oxidation, by, for example with an oxidizing agent or electric current, according to a method described herein. This discovery of autoantibodies in significant quantities in normal blood is previously unreported and, to the best of the inventor's knowledge, the existence of such autoantibodies in significant quantities in normal blood was completely unknown prior to the present invention.

The discovery of autoantibodies in significant quantities in normal individuals raises the question of why the autoantibodies are not detected in a standard assay (typically based on the binding of an antibody to its corresponding antigen) and why the autoantibodies do not cause disease symptoms in normal individuals.

In experiments described herein, it is shown that by the method of the present invention, autoantibodies can be obtained from biological fluids such as blood from a normal subject by exposing the biological fluid to an oxidizing agent or to a DC electric current, and that the process is reversible. Further, it was found that autoantibodies could be obtained by treating commercial IvIg products. Based on these experiments, a theory for how normal blood could contain autoantibodies without such antibodies being detected through ordinary screening procedures and without such antibodies causing disease is that the autoantibodies freely circulate along with other antibodies but that the antigen binding site of autoantibodies is somehow masked or inactivated in normal individuals. Because of the great quantity and variety of masked antibodies that are discovered according to the present invention, it is evident that such masked antibodies must play a role in healthy individuals. A beneficial role in such masked antibodies is supported by the finding of masked antibodies in human breast milk. Moreover, under the theory that the binding site of autoantibodies can be unmasked by a change in the redox state, it can be theorized that autoimmune diseases are triggered or aggravated by oxidation that unmasks the antigen-binding site of autoantibodies. Moreover, the discovery of masked autoantibodies in cerebral spinal fluid suggests that autoantibodies may be involved in neurodegenerative diseases such as Alzheimer's and Parkinson's diseases, which may be triggered or aggravated by unmasking of autoantibodies. It is known that nitrosylation of proteins in the CNS is one of the earliest measures of Alzheimer's onset. If this is going on in the brain, then this could also unleash the redox reactive autoantibodies to aPL. These aPL antibodies could in turn begin to interact with phospholipids in the brain and cause many of the lesions and shrinkage of the brain which is seen in MRI studies of the Alzheimer patient brains. Further, this theory suggests a more general mechanism by which the binding specificity of certain plasma proteins may be altered.

An immediate practical use of the discovery that forms the basis of the present invention is that it allows for an almost unlimited supply of the newly discovered autoantibodies to be obtained, which autoantibodies can be used as standards in diagnostic kits for the laboratory diagnosis of autoimmune and other aPL-related diseases. Previously, collection of large amounts of autoantibodies for commercial use has been difficult because it was thought that the autoantibodies had to be obtained from individuals having an autoimmune disease or testing positive for autoantibodies in standard assays. The amount of such blood that can be obtained from phlebotomy of individual patients or by pooling blood from a group of patients known to test positive for autoantibodies is limited. Other methods of obtaining autoantibodies, such as screening phage libraries as described in U.S. Pat. No. 5,885,793, may be difficult and time-consuming.

Testing blood samples for the presence or absence of masked antibodies may have important diagnostic value as it might presage or predict what antibodies could appear subsequent to oxidative stress in particular individuals

SUMMARY OF THE INVENTION

It is the object of this invention to provide a method of reversibly altering a binding specificity of a protein that has a binding specificity that can be reversibly altered by a change in its redox state.

It is a further object of the present invention to provide a method of obtaining autoantibodies from biological fluids such as blood, serum, plasma, raw milk, lymphatic fluid, or CNS fluid, particularly such fluids taken from normal individuals.

It is a further object of the present invention to provide a method of treating a subject having an autoimmune disease by administering to the subject an antioxidant sufficient to inactivate autoantibodies in said subject.

It is a further object of the present invention to provide a method of treating a subject having an autoimmune disease by inactivating autoantibodies of said subject extracorporeally.

It is a further object of the present invention to provide a isolated immunoglobulin that has a binding site that can be altered by a change in redox conditions and a product comprising a biological fluid or a protein-containing extract of a biological fluid that has been exposed to an oxidizing agent or a DC electric current sufficient to alter the binding specificity of at least one protein contained therein.

It is a further object of the present invention to provide a sample of a biological fluid from one or more persons who test negative for the presence of autoantibodies in routine clinical assays and which has been treated so that the biological fluid subsequently demonstrates the presence of autoantibodies.

These and other objectives are achieved by a method of altering a binding specificity of at least one protein in a biological fluid or in a protein-containing extract of a biological fluid, the protein having a binding site with a binding specificity that can be reversibly altered by a change in a redox state of the protein, by exposing the protein in the biological fluid or extract to an oxidizing agent or to a direct electric current (DC) to effect the reversible alteration of the binding specificity of the circulating protein.

The objects are further achieved by a method comprising the steps of providing a composition comprising at least one protein suspended or dissolved in a liquid medium, the protein having a binding specificity that can be altered by a change in its redox state, and exposing the composition to an oxidizing agent or a DC electric potential sufficient to effect the alteration of the binding specificity of the protein.

In another embodiment, the invention relates to a method of detecting or obtaining autoantibodies or other masked proteins from a biological fluid or from an extract of a biological fluid by exposing the autoantibody or other masked circulating protein in the biological fluid or extract to an oxidizing agent or to a DC electric current sufficient to alter the binding specificity of the autoantibody or other masked circulating protein so that the autoantibody or other masked circulating protein becomes capable of binding to an antigen or ligand, thereby becoming detectable and recoverable from the biological fluid or extract, and recovering the autoantibody or other masked circulating protein from the biological fluid.

In another embodiment, the present invention relates to an isolated immunoglobulin having a binding site with a binding specificity that can be reversibly altered by a change in the redox state.

In another embodiment, the present invention relates to a method of treating an autoimmune disease by administering to a subject having an autoimmune disease an amount of an antioxidant sufficient to inhibit or reverse an oxidative activation of binding sites of autoantibodies in the subject. A treatment of a person having an autoimmune disease may include extracorporeal treatment of the blood to reduce the unmasked proteins and replace them as masked proteins.

In another embodiment, the present invention relates to a method of screening a normal individual's biological fluid or extract to determine which autoantibodies are masked and thus construct a potential antibody profile of autoantibodies that could cause autoimmune disease in that individual if exposed or unmasked by oxidation or an electromotive force.

As a particular, non-limiting example, a biological fluid or extract such as an immunoglobulin mixture, may be exposed to an oxidizing agent or to a DC electric current to effect the alteration of the binding specificity of at least one autoantibody contained in the biological fluid or extract, so that the autoantibody becomes detectable in and recoverable from the blood, plasma, serum or extract.

BRIEF DESCRIPTION OF THE DRAWINGS

FIG. 1 is a table listing the particular antiphospholipid antibodies (aPL) that were assayed by the in-house enzyme-linked immunosorbent assay (ELISA) format used in many of the Examples, described below.

FIG. 2 is a table summarizing aPL assay results for a blood sample from a normal aPL-negative subject, incubated according to the method described in the opening section of the Examples.

FIG. 3 is a composite table summarizing aPL assay results of blood samples from seven aPL-negative normal individuals, incubated according to the method described in the opening section of the Examples.

FIG. 4 is a table summarizing aPL assay results for a serum sample from a normal aPL-negative subject, incubated according to the method described in the opening section of the Examples, with the feature that horse red blood cells (RBC) were substituted for human RBC in the procedure.

FIG. 5 is a table summarizing aPL assay results of an incubation of a serum sample carried out according to a method described in the opening section of the Examples, except that horse serum was substituted for human serum.

FIG. 6 is a table summarizing aPL assay results for a blood sample from a normal aPL-negative subject, incubated according to the method described in the opening section of the Examples, except that the incubation was carried out at room temperature (22° C.).

FIG. 7 is a table summarizing aPL assay results for a blood sample from a normal aPL-negative subject, incubated according to the method described in the opening section of the Examples, with the feature that 0.7 mm Degalan (plastic) beads were used as the particulate solid in the incubation mixture.

FIG. 8 is a table summarizing aPL assay results for a blood sample from a normal aPL-negative subject, incubated according to the method described in the opening section of the Examples, except that the incubation mixture was kept stationary, instead of being shaken or rocked.

FIG. 9 is a table summarizing aPL assay results for a blood sample from a normal aPL-negative subject, incubated according to the method described in the opening section of the Examples, with the added feature that the incubation mixture was heated to 56° C. for 30 minutes.

FIG. 10 is a table summarizing aPL assay results for a blood sample from a normal aPL-negative subject, incubated according to the method described in the opening section of the Examples, with the feature that a bacterial culture growth medium from a different supplier (Becton Dickinson, Sparks, Md.) was used in place of the bacterial culture growth medium from Biomerieux.

FIG. 11 is a table summarizing aPL assay results for a blood sample from a normal aPL-negative subject, incubated according to the method described in the opening section of the Examples, with the feature that the incubation occurred under anaerobic conditions.

FIG. 12 is a table summarizing aPL assay results for a blood sample from a normal aPL-negative subject, incubated according to the method described in the opening section of the Examples, with the feature that K562 cells (a human tumor cell line) were used instead of RBC.

FIG. 13 is a table summarizing aPL assay results for a blood sample from a normal aPL-negative subject, except that the bacteria culture growth medium was replaced with a cell culture medium used for growing human cells.

FIG. 14 is a table summarizing aPL assay results for a cord blood sample from a normal aPL-negative mother and baby.

FIG. 15 is a table summarizing aPL assay results for a blood sample from a normal aPL-negative subject, incubated according to the method described in the opening section of the Examples, with the feature that sodium nitroprusside (SNP) was used in place of RBC in the incubation mixture.

FIG. 16 is a table summarizing results of a lupus anticoagulant activity assay for a blood sample incubated according to the method described in the opening section of the Examples. The blood sample was obtained from a subject whose blood is lupus anticoagulant negative prior to seroconversion by the present invention process.

FIGS. 19 A-D are flow cytometry histograms showing monocyte activity of various sera. In the histograms, antibody activity, if present, is measured by shifts in the median channel values (log scale) along the horizontal axis.

FIG. 20 is a table summarizing the results of anti-nuclear-antibody (ANA) testing of various samples using a RELISA® screening assay.

FIG. 21 is a table summarizing aPL assay results for a sample of IvIg that was incubated with hemin in a tris buffer.

FIG. 27 shows the Western blots obtained for three cell lysates with hemin-treated IvIg and untreated IvIg used as primary antibodies, along with a blot wherein anti-human HRP-tagged conjugate was used as a control.

FIGS. 28A and 28B are graphs showing the amount of aPL dependent and aPL independent aPS, aCL, aPE, and aPC (as measured by multiples of the mean, MoMs) detected in a series of IvIg preparations in which electrodes connected to a 9 volt battery were immersed in a phosphate buffered saline solution containing the IvIg for 2 minutes.

FIGS. 38 A-D are flow cytometry histograms showing neutrophil activity of various IvIg preparations.

DETAILED DESCRIPTION OF THE INVENTION

Figures 17, 18:
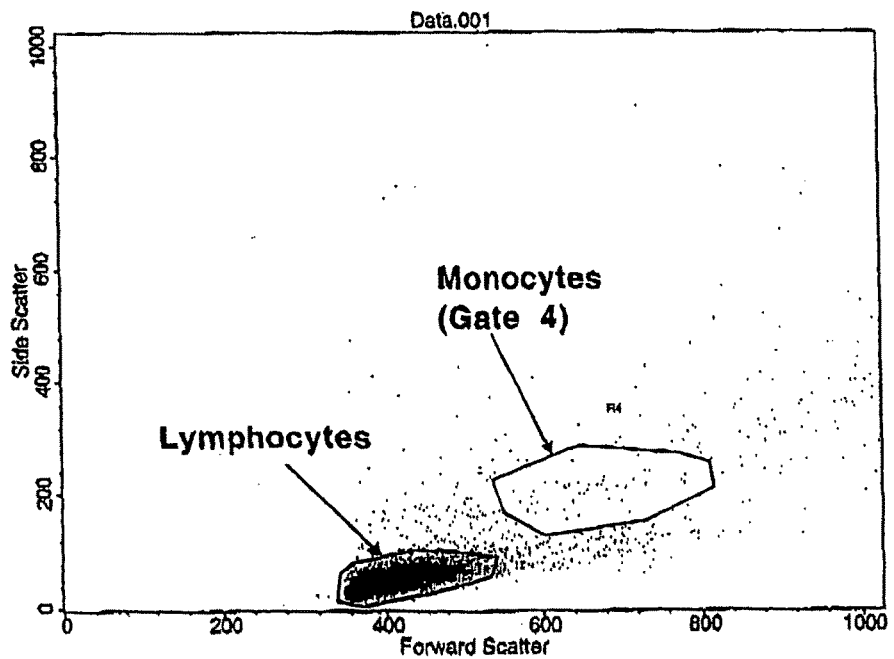
FIG. 17 is a table listing other types of autoantibodies that have been identified in blood samples that are incubated according to the method described in the opening section of the Examples. The listed antibodies were identified by immunofluorescence microscopy.
FIG. 18 is a graph showing the forward scatter (size) and side scatter (granularity) profile of the monocyte population of cells as defined for density gradient isolated human white blood cells by flow cytometry.

The present invention relates to a method of altering the binding specificity of at least one protein in a biological fluid or extract of a biological fluid.

Typically, proteins that are the subject of the present invention are those that are naturally found in the circulation system, lymphatic system, cerebral spinal fluid or breast milk of animals. Examples of such proteins include antibodies and other plasma proteins. As a non-limiting example, the protein may be an antibody or an autoantibody of the IgG, IgA or IgM isotype. In particular, the present invention is directed to a class of proteins as newly discovered herein that have the property of having a binding specificity that can be reversibly altered by a change in the redox state of the protein. The discovery by the inventor that there are circulating proteins, such as autoantibodies, that have this property forms a basis of the invention. The present invention is not limited to antibodies or autoantibodies, since it has also been discovered that certain non-antibody proteins have a binding specificity that can be altered by a change in the redox state. These non-antibody proteins include kininogen and prothrombin and/or beta2 glycoprotein.

The term "masked protein" is used herein to designate and describe a protein such as a circulating protein that, in normal individuals, is present in the blood or other bodily fluids, but is not detectable by conventional binding assays based on receptor-ligand binding because its binding site is, in the normal individual or in a sample taken from the normal individual, masked or blocked or otherwise prevented from binding an antigen, and that, when a sample containing the masked protein is treated by changing its redox state, such as by exposure to an oxidizing agent or electric current according to a method of the present invention, becomes capable of binding an antigen and thereby becomes detectable in a sample. An example of a masked protein is an autoantibody according to the present invention, including, but not limited to those that are listed in Table 2, below. As discovered by the present inventor, masked autoantibodies circulate in significant quantities in normal blood, but they are not detectable in conventional assays based on antibody-antigen binding. As discussed herein, a masked autoantibody becomes detectable and recoverable when the autoantibody is subjected to oxidation-reduction conditions sufficient to alter its binding specificity.

After the discovery that forms the basis of the present invention, it has been possible to screen samples such as blood, serum, breast milk, cerebral spinal fluid, and IvIg extracts with a variety of self antigens and other types of antigens to identify masked autoantibodies that can be unmasked by oxidation. Autoantibodies that have been unmasked by oxidation include the following in Table 2:

TABLE 2

Masked autoantibodies identified to date after redox conversion of normal plasma or IgG.

| Specificity Assay | Method | Comment |
|---|---|---|
| Glutamic acid decarboxylase (GAD) | RIA | Very strong |
| Tyrosine phosphatase (IA-2) | RIA | Intermediate |
| Antiphospholipid antibodies: aPS, aPE, aCL, aPC strong aCL, weak aPC | ELISA | Very strong aPS, aPE, |
| Lupus anticoagulant (LA) | APPT, dRVVT | Intermediate to strong |
| Antinuclear antibodies (ANA) | RELISA ® | Very strong |
| Anti-nucleolus | immunofluorescence | Strong |
| Anti-lamin, nuclear membranes | immunofluorescence | Very strong |
| Anti-mitochondria | immunofluorescence | Intermediate |
| Anti-Golgi | immunofluorescence | Intermediate |
| Anti-granulocyte, neutrophil, monocyte | Flow Cytometry (FACS) | Very strong |
| Anti-B lymphocytes | FACS | Intermediate |
| Anti-myeloperoxidase | ELISA | Very strong |
| Anti-tumor cell lines | Western blot | Very strong |
| Anti-trophoblast | immunofluorescence | Very strong* |
| .Anti-HLA | ELISA and FACS | Negative |
| Anti-factor VIII | ELISA | Strong positive |
| Platelet factor 4/heparin complex | ELISA | Strong Positive |
| Anti-beta2-glycoprotein I | ELISA | Strong Positive |

*Trophoblast basement membrane reactivity strikingly similar to that reported by Faulk et al. using placental eluates [27].
Table 2 abbreviations used:
aCL, anticardiolipin
aPC, antiphosphatidylcholine
aPE, antiphosphatidylethanolamine
aPS, antiphosphatidylserine
APPT, activated partial thromboplastin time
dRVVT, dilute Russell's viper venom time
ELISA, enzyme-linked immunosorbant assay
RIA, radioimmunoassay Accordingly, the present invention includes methods of altering the binding specificity of any of the above immunoglobulins from a non-binding status to a binding status with respect to their particular antigen. Moreover, it is believed that the above immunoglobulins that are unmasked by the methods of the present invention represent a previously undiscovered class of autoantibodies. Accordingly, the present invention further includes isolated immunoglobulins that have an antigen binding site with a binding specificity that can be reversibly altered by a change in the redox state. The term "isolated immunoglobulin" refers to an immunoglobulin that has been removed from its natural state. For example, an immunoglobulin of the present invention is typically one that was previously undetectable in a biological sample because its antigen binding site was maintained in its natural environment in a non-binding status. However, with treatment of the sample to change the redox state, such as treatment with an oxidizing agent or DC electric current, the immunoglobulin becomes capable of specific binding of a particular respective antigen. By exploiting the changed ability of the immunoglobulin to specifically bind a particular antigen, the immunoglobulin can be detected, isolated and/or recovered from the sample.

Further, it has also been found that blood, serum or IvIg samples that initially test negative for HCV (hepatitis C virus) tests positive for HCV after a treatment according to the present invention, suggesting that normal individuals have masked anti-HCV antibodies in their circulation.

The term "altering the binding specificity" of a protein refers to a process whereby a protein is changed or altered, such as by oxidation or reduction, so that it becomes capable of specific binding of an antigen or ligand that it had not previously been capable of specifically binding. The term may also apply to a process whereby a protein is changed or altered, such as by oxidation or reduction so that it becomes incapable of specific binding of an antigen or ligand that it had previously been capable of specifically binding, but it is to be understood that in this context, the term refers to a reversible change and not a permanent, irreversible change such as denaturation of the protein. The term "unmasking" refers to a process wherein the binding specificity of a masked protein is altered by a change in redox state so that the protein becomes detectable by a binding assay based on the altered binding specificity. In particular, the binding specificity of the masked protein may be changed from a non-binding status to a binding status with respect to an antigen or ligand, whereby the protein is considered to be unmasked.

The term "autoantibody" refers to any naturally occurring antibody produced by the immune system of an animal and that binds to a self-antigen, that is, to a compound or antigen produced by the animal itself.

The terms "bodily fluid" or "biological fluid" includes any bodily fluid including plasma, serum and whole blood, saliva, urine, lactation fluids, central nervous system (CNS) fluid, such as cerebral spinal fluid and other fluids and secretions and that may proteins such as circulating proteins. The bodily fluid may be from any vertebrate that produces antibodies, particularly mammals and birds and most particularly humans. The term "protein-containing extract of a biological fluid" refers to any preparation that is collected or separated from a biological fluid, such as immunoglobulin fractions. Biological fluids including blood, serum or plasma that may be used in the present invention may be freshly obtained from an subject, or may be obtained from such sources as pooled blood or plasma preparations obtained from blood banks or other blood collection facilities. For the purposes of the present invention, blood, serum or plasma may also be from collections that are out-of-date or otherwise found to be substandard by blood banks or blood collection facilities. Although this description focuses upon human blood, plasma and serum and other biological fluids, the identical process of this invention can be applied to biological fluids obtained from animals and should result in obtaining analogous animal antibodies for purposes relating to veterinary medicine. For example, analogous autoantibodies have been detected in samples from horses and chickens (data not shown). Preferably, biological fluids used in the method of the invention may be diluted to reduce the effect of any antioxidants that may be contained therein.

Moreover, the method of the present invention may be carried out on an extract such as an IvIg preparation or any other isolated extract or concentration of immunoglobulins. As detailed in the Examples, below, such preparations when they are untreated, show minimal levels of autoantibodies. Masked proteins such as masked autoantibodies may be detected and recovered from such preparations upon treatment with an oxidizing agent or DC electric current according to a method of the present invention.

In the method of the present invention, the binding specificity of at least one circulating protein or plasma protein in a biological fluid is altered by exposing the protein to an oxidant or to an electric current. For example, the binding specificity of a masked circulating protein can by altered so that the protein is unmasked, that is, so that it is able to bind an antigen that it was not able to bind before the method was carried out. A protein that has had its binding specificity altered may then be isolated and recovered by any separation method based on specific binding.

If an oxidizing agent is used to carry out the method of the invention, the oxidizing agent can be any compound that is capable of altering the redox state of a biological molecule. More specifically, the oxidizing agent is a molecule that has the ability to be reduced by acting as an electron acceptor for other molecules that act as electron donors. Suitable oxidizing agents include ring compounds that contain a coordinated metal, particularly an oxidizing metal such as iron. Examples of oxidizing agents include, but are not limited to hemin and chlorophyll. Other oxidizing agents include potassium permanganate ($KMnO_4$). Typically, when an oxidizing agent is used, a mixture of the biological fluid or extract and the oxidizing agent must be incubated for a period of time, typically for about a day or overnight. The oxidizing agent should be used at a concentration sufficient enough to alter the binding specificity of a protein having an alterable binding specificity, but not at a concentration that might destroy or denature the protein. In the case of autoantibodies, it has been found that different types of autoantibodies can interact differently with different antioxidants. For example, for the unmasking of aPC autoantibodies, the results are very good with $KMnO_4$ and not as good with hemin.

If a DC electric current is used to carry out the method of the invention, the method may be carried out by any means of delivering an electric current, such as by immersing positive and negative electrodes into a conductive solution containing the sample to be treated. Typically, a solution containing a biological fluid may be exposed to an electric potential of a sufficient magnitude and of a sufficient duration to alter the binding specificity of a protein having an alterable binding specificity. It has been found that positive results may be obtained by exposing a solution to an electric potential of 6-24 volts for a few seconds to a few minutes. As discussed in the examples, an extended exposure to an electric current may result in reversibility of the alteration of the binding specificity.

Without being bound to a specific theory, it is preferred, in the case of an autoantibody, that the autoantibody be exposed to the oxidizing agent or electric current in an amount or for a time sufficient to oxidize an antigen binding site in a Fab portion of the autoantibody. It has been found by further experiments using detection by anti-nitrotyrosine antibodies that IgG that has been exposed to oxidation by hemin has a greater degree of nitrosylation than non-treated IgG. Accordingly, it can be theorized that the alteration of the antigen binding site of proteins, and particularly the alteration of the antigen binding specificity of autoantibodies is effected by reversible nitrosylation of tyrosine residues in and around the antibody hypervariable region, which may produce conformational changes in the antigen binding site.

Whether a particular protein of interest is one that has a binding specificity that can be altered by changing its redox state and the effectiveness of any set of conditions for altering the binding specificity of the particular protein of interest may be readily determined by subjecting the protein or a biological fluid containing a protein to a change in redox state by, for example, exposing the protein or biological fluid to an oxidizing agent and then using ELISA or other ligand-receptor assays to determine whether the binding specificity of the protein has been altered. In otherwords, an assay of a sample or of a series of samples taken from a subject can be carried out before and after a protein is subjected to a change in redox conditions to see whether the process has altered the binding specificity of the protein. For example, the best oxidizing agent to recover a specific autoantibody can be readily determined by simple experimentation.

A further aspect of the present invention is the possibility of treating a subject having an autoimmune disease, based on a new understanding of how these diseases may arise. For example, if it is known that autoimmune diseases arise by the unmasking of autoantibodies that are present in a masked form in healthy individuals, then treatment and prevention can focus on inhibiting or reversing the unmasking of autoantibodies, such as by treating the subject with an antioxidant or reducing agent to cause autoantibodies to revert to a masked state. Agents that have been found to inhibit an unmasking reaction of autoantibodies include antioxidants such as ascorbic acid, hemopexin and apotransferrin. Similarly, a treatment method may include taking a blood sample from the subject, exposing the blood sample to an antioxidant, reducing agent or electric current sufficient to inactivate autoantibodies in said blood sample, and returning the blood sample to the subject.

A further aspect of the present invention is a method of screening an individual's biological fluid or extract to determine which autoantibodies are masked and thus construct a potential antibody profile of autoantibodies that could cause autoimmune disease in that individual if exposed or unmasked by oxidation or an electromotive force. For example, in general terms, a biological sample from a subject can be assayed to determine an amount and/or type of autoantibodies detectable in the sample. Thereafter, a biological sample from the subject can be treated by exposing the sample to an oxidizing agent or a DC electric current, and the sample from the subject can be assayed to determine an amount and/or type of autoantibodies detectable in the treated sample. Thereafter, the amount and/or type of autoantibodies detectable in the sample before the treating step can be compared with the amount and/or type of autoantibodies detectable in the sample after the treating step. These same method steps can be carried out to determine the effectiveness of any particular compound, composition or conditions for achieving an alteration of a binding site of proteins in any particular sample.

It has been found that untreated blood, plasma, serum or IvIg samples and blood, plasma or serum or IvIg samples treated according to the method of the present invention can be lyophilized and shipped or stored. When the samples are reconstituted, they retain their respective activity.

EXAMPLES

Having described the invention, the following examples are given to illustrate specific applications of the invention, including the best mode now known to perform the invention. The examples are presented in approximate chronological order and thus show a progression in the understanding of components and procedures required to achieve the effects of the invention. These specific examples are not intended to limit the scope of the invention described in this application.

Regarding each of the Examples 1-17 described herein, unless otherwise noted, the following procedure was typically used: A 10 ml sample of whole blood or 5 ml of serum or plasma from a normal aPL-negative subject and 4-5 ml of packed mammalian red blood cells were added to a vial containing 30 ml of Biomerieux brand bacterial culture growth medium (containing at least the following ingredients: distilled water, soybean-casein digest broth, yeast extract; dextrose; sucrose; hemin; menadione (vitamin K3); pyridoxal HCl (vitamin B6); and sodium polyanetholesulfonate (SPS) and charcoal. Then, the mixture was incubated, with rocking or shaking, at 37° C. for a period of 18-22 hours. Following the incubation and centrifugation, a sample of the incubated blood or serum/RBC was tested for the presence of antiphospholipid antibodies (aPL) using a comprehensive in-house ELISA aPL format that provides 24 separate aPL test results. The testing procedure is described in greater detail in the following publications, incorporated herein by reference: Wagenknecht D R, et al., The Evolution, Evaluation and Interpretation of Antiphospholipid Antibody Assays, Clinical Immunology Newsletter, Vol. 15, No. 2/3 (1995) pp. 28-38 and McIntyre J A, et al., Frequency and Specificities of Antiphospholipid Antibodies (aPL) in Volunteer Blood Donors, Immunobiology 207(1): 59-63, 2003.

FIG. 1 shows the 24 separate aPL specificities that were tested for by using the comprehensive in-house ELISA aPL format. Four specificities were assessed, 1) aPS=antiphosphatidylserine, 2) aCL=anticardiolipin, 3) aPE=antiphosphatidylethanolamine, and 4) aPC=antiphosphatidylcholine. For each of these aPL specificities, three immunoglobulin isotypes were sought, IgG, IgA and IgM. Each specificity and each isotype were assessed in the presence (dependent) and absence (independent) of a buffer diluent supplement, 10% adult bovine plasma (ABP), which contains the phospholipid-binding plasma proteins) or 1% bovine serum albumin, (BSA, which is devoid of phospholipid-binding plasma proteins), respectively. The final dilution of the subjects' blood samples was between 1/50 and 1/100.

The results in the 24 aPL specificities obtained for the various experiments described herein are given in the accompanying figures. The positive/negative findings are expressed in multiples of the means (MoM) based on testing plasma samples from 775 normal blood donors, as described in McIntyre J A, Immunobiology, above. The presence of +++ indicates strong antibody activity. The markers of + and ++ indicate low and intermediate antibody activity, respectively. The figures also provide the normal range values for each aPL specificity and isotype combination.

A positive result in the column indicated as PL binding protein "dependent" means that the antiphospholipid antibody (aPL) is actually binding to a plasma protein that initially has bound to the particular phospholipid indicated. Plasma proteins that typically can be bound by PS and CL include the following: beta$_2$-glycoprotein I, prothrombin, protein C, protein S, annexin V, and complement components Factor H and C4 (see, for example, McIntyre, J. A., Wagenknecht, D. R. and Faulk, W. P. Antiphospholipid antibodies: Discovery, definition, detection and disease. Prog. Lipid Res. 42(3): 176-237, at page 182). The physiological nature of the plasma protein binding is not known precisely for all of the phospholipids, but such binding is thought to induce conformational changes in the plasma protein structure, thereby exposing novel or cryptic epitopes that then are targeted by the individuals' autoantibodies. Plasma proteins that typically can be bound by phospholipid PE include the following: high and low molecular weight kininogens, and factor XI and prekallikrein. The latter two proteins can be detected by virtue of their fidelity in binding to high molecular weight kininogen. The plasma proteins that bind to PC have not yet been defined. In certain experiments, plasma-protein independent aPL are observed (see FIG. 3). A possible explanation for this activity is that it represents the presence of residual phospholipid-binding plasma proteins that are present in the original blood sample.

Example 1

A sample of blood from a normal subject was incubated and tested according to the procedure described above. The results of the aPL ELISA are shown in FIG. 2. As shown in FIG. 2, the incubated blood sample shows a dramatic presence of autoantibody activity, in comparison to the normal, untreated blood shown in the Normal ranges column. In particular, strong autoantibody activity is shown in the protein-dependent category for aPS (IgG), aCL (all isotypes), and aPE (IgG). The low or absent IgG aPC autoantibody activity was a characteristic finding in the early examples and in procedures in which hemin was used as the oxidizing agent. This result indicates that autoantibodies to PC, especially of the IgG isotype are different and perhaps do not become activated in the same way as do the others. In later experiments, it was found that significant levels of aPC can be detected in samples that were treated with $KMnO_4$ (data not shown).

Example 2

Blood samples drawn from seven healthy subjects were incubated and tested according to the procedure described above. In particular, all seven subjects' bloods were drawn within a 20 minute period and incubated for 20 hours in identical conditions. FIG. 3 is a composite table showing the range of aPL seroconversion for these seven samples. These results show that there are variations in the aPL levels detected as well as the isotypes present among different individuals. Nevertheless, as shown by the invention, each individual had aPL antibodies that could be detected after incubation.

Example 3

In a first experiment, a serum sample from a normal subject was incubated and tested according to the basic procedure described above. In the incubation mixture, horse red blood cells (RBC) were used instead of human RBC. The results of the aPL ELISA are shown in FIG. 4. As shown in FIG. 4, significant aPL activity was obtained, particularly with respect to aPS (IgG and IgM) and aCL (IgA and IgM).

In a second experiment, a horse serum, instead of human serum, was incubated with human RBC and tested according to the basic procedure described above. The results of the aPL ELISA are shown in FIG. 5. As shown in FIG. 5, aPL activity was not obtained. (The ELISA assay used in this experiment utilized human-antibody-specific alkaline phosphatase labeled antibody probes to detect aPL, so whether the incubated sample contained horse aPL is unknown.)

The results shown summarized in FIGS. 4 and 5 unequivocally demonstrate that all aPL that are obtained during the seroconversion process of the present invention originate from the human serum and are not released from the human RBC, since the first experiment uses horse RBC, which are devoid of human antibodies, in place of human RBC and still shows positive results, whereas the second experiment uses horse serum in the presence of human RBC and shows negative results.

Example 4

A blood sample from a normal subject was incubated and tested according to the basic procedure described above, except that the incubation was carried out at room temperature (22° C.), instead of at an elevated temperature. FIG. 6 shows that the sample did not undergo seroconversion when incubated at room temperature. These results suggest that the process of seroconversion may be temperature sensitive.

Example 5

A blood sample from a normal subject was incubated and tested according to the basic procedure described above, with the feature that 0.7 mm Degalan (plastic) beads were used as the particulate solid in the incubation mixture instead of charcoal. Since charcoal was used in initial experiments showing seroconversion, this experiment was carried out to determine whether charcoal plays a specific role in the seroconversion. FIG. 7 shows that the sample exhibited seroconversion even when plastic beads were used in place of charcoal. These results suggest that the role of charcoal is mechanical, rather than chemical, in nature, and that any particulate solid, such as plastic, resin or glass beads, can be used. Without being limited to any particular theory, it can be theorized that the particulate component acts as an abrasive upon the RBC membrane, probably causing release of the NO ion from the RBC, either by interacting with the RBC AE1/Band 3 protein or with the SNO-hemoglobin transition molecules or both. The possibility of mechanical abrasion is supported by the observation in Example 6, wherein negative assay results are shown for an incubation mixture that is not rocked or shaken. The particulate solids may also serve a mechanical function of assisting autoantibody release.

Example 6

A blood sample from a normal subject was incubated and tested according to the basic procedure described above except that the incubation mixture was kept stationary, instead of being shaken or rocked. FIG. 8 shows that the sample did not undergo seroconversion when it was kept stationary. These results suggest that movement may facilitate interaction between solid particles and RBC. Stationary incubation conditions did not facilitate aPL release, although a small amount of movement such as produced by transport of the samples to the incubator may produce small amounts of aPL release.

Example 7

A blood sample from a normal subject was incubated and tested according to the basic procedure described above, with the added feature that after incubation and removal of RBC and charcoal by centrifugation, the incubation mixture was heated to 56° C. for 30 minutes. FIG. 9 shows that the amount of detected aPL was significantly increased by this procedure.

Example 8

A blood sample from a normal subject was incubated and tested according to the basic procedure described above, with the feature that a bacterial culture growth medium from a different supplier (Becton Dickinson, Sparks, Md.) was used in place of the bacterial culture growth medium from Biomerieux. FIG. 10 shows that the sample exhibited seroconversion in the Becton Dickinson medium, indicating that the method of the present invention is not dependent upon a bacterial culture growth medium from a particular source.

Example 9

A blood sample from a normal subject was incubated and tested according to the basic procedure described above, with the feature that the incubation occurred under anaerobic conditions (under nitrogen) instead of under aerobic conditions (in the presence of oxygen and $CO_2$). FIG. 11 shows that the sample exhibited seroconversion even under anaerobic conditions and that the method of the present invention is not dependent upon an aerobic environment.

Example 10

A blood sample from a normal subject was incubated and tested according to the basic procedure described above, with the feature that K562 cells (a human hematopoetic tumor cell line) were used instead of red blood cells. Further, only 11.3 million K562 cells were present in the culture media, compared to 3-4 mls of packed RBC typically used in the method of the invention. FIG. 12 shows that the sample exhibited seroconversion.

Other experiments have shown that samples that are incubated with other isolated cell types, lymphocytes, monocytes and neutrophils typically do not exhibit aPL seroconversion. In particular, white blood cells of the lymphoid and myeloid series did not support aPL release, nor did a cell line of porcine B lymphocytes designated as L14 (data not shown). These results suggest that hemoglobin may be a key component in the incubation mixture, since K562 cells and RBC contain hemoglobin, and lymphocytes, monocytes and neutrophils do not.

Example 11

A blood sample from a normal subject was incubated and tested according to the basic procedure described above, except that the bacteria culture growth medium was replaced with a cell culture medium used for growing human cells: RPMI. FIG. 13 shows that seroconversion did not occur. This experiment shows the importance of some ingredient in the bacterial culture media for the purpose of this invention. While RPMI is a culture media designed for human cells, it does not support aPL release when substituted for vial broth. Listings and comparisons of the ingredients in the two different microbiology vial broths with RPMI show that RPMI lacks hemin and menadione (a man-made provitamin K) called vitamin K3. It is known that hemin is a porphyrin chelater of iron (Fe+++) derived from RBC, and menadione is a fat-soluble vitamin. This indicates that redox reactions may play a role in autoantibody release

Example 12

A placental cord blood sample incubated and tested according to the basic procedure described above. The placental cord blood was drawn after the birth of the baby, but before the placenta was detached from the uterine wall. Neither the mother's blood nor the baby's cord blood showed the presence of aPL in conventional laboratory assays. When processed according to the invention described herein, strong aPL antibody was demonstrated present in the cord blood samples, as shown in FIG. 14. The antibodies were IgG only, an observation that is compatible with antibodies of maternal origin. Since the mother transports IgG to the fetus prior to birth, this experiment seems to indicate that the masked maternal autoantibodies transported to the fetus by way of specialized Fcγ receptors on the trophoblast (FcγRn) remain masked by the fetus in the fetal blood. Since the mother's blood and the cord blood were shown to be aPL-negative prior to seroconversion by the method of the invention, and since there were no IgM or IgA immunoglobulins detected, these findings support the contention that the IgG aPL observed in the cord blood subsequent to seroconversion are maternal in origin. It also is of interest that the trophoblast that expresses the FcγRn does not express HLA antigens.

Example 13

A plasma sample from a normal subject was incubated and tested according to the basic procedure described above; with the feature that sodium nitroprusside (SNP, 200 micromolar) was used in place of RBC in the incubation mixture. FIG. 15 shows that the sample exhibited seroconversion.

Since SNP is a potent nitric oxide (NO) donor, these results provide supportive evidence that the NO radical is involved in the autoantibody release and further support a theory that RBC and solid particulates fulfill a role of providing $NO^-$ donation from the RBC. Other free radical mediated reactions apart from sodium nitroprusside may also cause autoantibody release.

Example 14

A blood sample from a normal subject was incubated according to the basic procedure described above and was tested for lupus anticoagulant activity. Lupus anticoagulant or inhibitor is another type of aPL and is typically detectable only by functional laboratory assays. The results in FIG. 16 show a strong lupus anticoagulant (LA) in the seroconverted blood taken from a lupus inhibitor negative individual and processed by the method of this invention. While initially corrected by adding normal plasma to the seroconverted broth in the dRWT assay, incubation for 1-2 hours resulted in the reappearance of the inhibitor. This time frame is proposed as the time it takes for the LA or unmasked antibodies to bind the relevant phospholipid-binding plasma proteins introduced by the mixing study. It also rules out the possibility of clotting factor deficiencies since a 1:1 mix provides sufficient levels of clotting factors to correct clotting times in a factor deficient sample. The dilute prothrombin time (dPT) did not correct in the presence of normal plasma and increased prolongation of clotting times was observed after incubation with normal plasma, which is indicative of a strong lupus inhibitor.

Example 15

Blood samples from five normal subjects were incubated according to the basic procedure described above and were tested by fluorescence microscopy for the presence of other types of autoantibodies. Sera and plasma samples from these five individuals were negative prior to processing according to the teachings of the invention. FIG. 17 lists additional autoantibody specificities identified by using the Hep-2 cell line. Identified were anti-nucleolar (scleroderma associated), anti-lamins (very bright at nuclear pores), anti-mitochondrial (cytoplasmic), and anti-centriole. The results show that autoantibodies released by the method of the present invention can also be detected by a different methodology of detection, fluorescence microscopy, as opposed to ELISA-based testing. The results confirm that many types of autoantibodies besides aPL are masked in the blood of individuals whose serum and plasma test negative for these antibodies in routine laboratory analyses.

From these results, it can be expected that many more autoantibody specificities await to be found by testing bloods processed by this invention.

Example 16

Figure 19A:
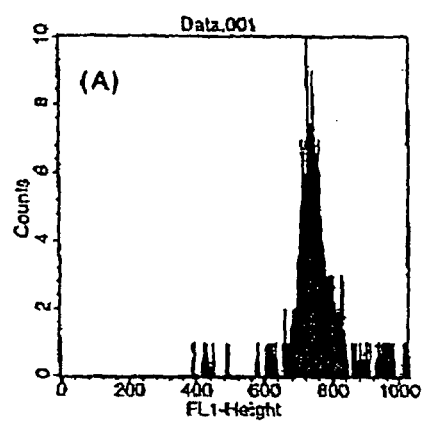
FIG. 19A shows monocyte reactivity of pooled normal human sera (NHS).
Figure 19B:
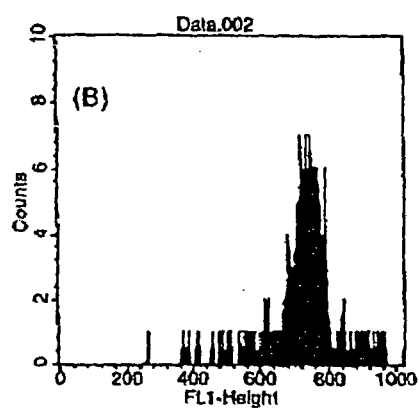
FIG. 19B shows the monocyte activity of a serum from a single normal subject.
Figure 19C:
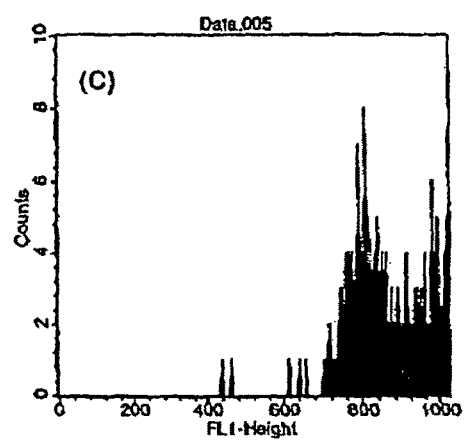
FIG. 19C shows the monocyte activity of a blood sample from the subject shown in FIG. 19B that was treated according to the method described in the opening section of the Examples.
Figure 19D:
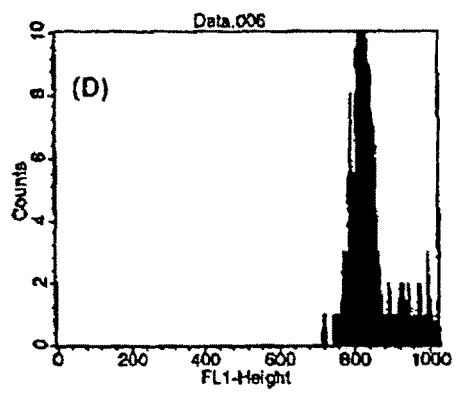
FIG. 19D shows the monocyte activity of positive control sera.

A blood sample from a normal subject was incubated according to the basic procedure described above and was tested for reactivity with monocytes using flow cytometry and fluorescent conjugated antihuman IgG antibodies. Comparative testing was done with untreated-pooled normal human sera (NHS), with serum from the same normal subject used with the invention and with positive control human sera. (The treated blood showed no auto reactivity with lymphocytes and neutrophils; these data are not shown.) FIG. 18 depicts the forward scatter (size) and side scatter (granularity) profile of the normal subject's monocyte population of cells as defined by flow cytometry. This monocyte population of cells was confirmed by showing reactivity with CD 14 monoclonal antibodies. FIG. 19A shows anti-monocyte reactivity with NHS. The median reactivity shown is 743.50 on a linear scale. FIG. 19B shows the auto-anti-monocyte activity of the normal subject's serum; this subject does not have antibody activity to autologous monocytes. The median reactivity shown is 737.00. FIG. 19C shows the auto-anti-monocyte activity of a blood sample from the subject shown in FIG. 19B after it is treated according to the method of the invention. The median value is shown is 864.00, indicating strong auto-anti-monocyte activity. Despite the fact that the plasma processed according to the teachings of the invention were used at a dilution of ⅛, it showed more reactivity with monocytes than did the undiluted positive control sera. Thus, this example shows that blood or serum samples processed according to the method of this invention release autoantibodies that specifically target monocytes. The same results were documented for four additional samples from other individuals when processed according to the teachings of the invention.

Example 17

Comparative tests for the presence of anti-nuclear-antibodies (ANA) using a RELISA® screening assay were carried out on untreated cord blood serum; cord blood incubated according to the method of the present invention, with no rocking; cord blood treated according to the method of the present invention, with rocking; untreated serum from an ANA-negative healthy donor (identified as ACS) and serum from the same ANA-negative healthy donor that was incubated according to the method of the present invention. As shown in FIG. 20, a significant amount of ANA was identified in cord blood and serum samples that were treated by the method of the present invention. From the results in FIGS. 16 and 17, it can be expected that many more autoantibody specificities wait to be found by testing bloods processed by this invention.

Example 18

To understand the role of red blood cells in the phenomenon of autoantibody release, experiments were designed to replace the red blood cells with simpler ingredients that might mimic the action of the red blood cells. In the present experiment, the red blood cells and charcoal were replaced with sodium nitroprusside (SNP) and ferric chloride. This substitution was made because sodium nitroprusside is a powerful nitric oxide producer, and it is known that the RBC are carriers of $NO^-$. Ferric chloride ($FeCl_3$ stock solution, 25 uM), was added as a substitute for the iron in hemoglobin.

Culture bottles containing the bacterial culture growth medium and 5 ml of human plasma or serum and varying concentrations of sodium nitroprusside (SNP, 200 μm) and exogenous ferric chloride (4.1 μm final concentration) was used in place of red blood cells and charcoal, were incubated at 37° C. and then heated to 56° C. for 30 minutes. The samples showed seroconversion of aPL, but only IgG (data not shown).

The results suggest that $NO^-$ may be involved in antibody unmasking, and suggest that the mechanical action of a solid phase material in the culture bottle disrupts the red blood cells and releases $NO^-$. Alternatively, the release or modification of NO may enable the hemoglobin molecule to participate in redox reactions.

Example 19

In an effort to determine whether the effect of unmasking autoantibodies was due to the breakdown of autoantibody-containing macromolecular structures within serum or blood or whether it was due to direct changes in the binding specificity of antibodies themselves, a series of experiments were carried out in which commercial intravenous immunoglobulin (IvIg) was substituted for human plasma or serum. Commercial IvIg is an alcohol precipitate fraction of pooled plasma from multiple donors, typically from 1,000-10,000 donors. Typically, IvIg contains primarily IgG, and is mostly devoid of IgA, IgM and other plasma proteins. When untreated IvIg is tested for the presence of autoantibodies by ELISA testing, the test results are negative. Because of its manner of preparation, IvIg is also free of lipoprotein micelles, vesicles or other macromolecular structures. Therefore, if IvIg were to test positive for the presence of autoantibodies after an incubation treatment, it would have to be that the autoantibodies were obtained by an alteration of IgG antibodies already present in the IvIg preparation and not by a breakdown of structures or vesicles concealing the autoantibodies.

In the examples that follow, the commercial preparation of IvIg used was lyophilized IvIg (Immune Globulin Intravenous (Human) Gammar-PI.V., Aventis Behring, Kankakee, Ill.).

A 5 gram commercial preparation of lyophilized IvIg was reconstituted in sterile phosphate buffered saline (PBS, 100 mg/ml). 1.7 ml of the reconstituted IvIg solution was added to a culture bottle containing the bacterial culture growth medium (without red blood cells or charcoal) and was incubated at 37° C. for 20 hours. The incubated mixture showed seroconversion and the presence of aPL IgG (data not shown). (As expected, only IgG was detected, not IgA or IgM.)

In similar experiments, autoantibodies were detected in a mixture that was incubated at room temperature in a shaking vial, but the results were not as good as at 37 degrees (results not shown).

Heating the IvIg-bacterial growth medium mixture above 37° C. did not result in further increases in autoantibodies.

As a control, IvIg straight out of the bottle was tested for aPL and other autoantibodies, and the results were negative.

Example 20

In Example 19, it is shown that autoantibodies can be obtained by incubating a commercial IvIg preparation in a bacterial growth medium. The next step was to try to determine which ingredients in the bacterial culture growth medium play a role in producing detectable autoantibodies.

First, IvIg in 2% tryptic soy broth (TSB), (which contains peptones in a 17 to 3 ratio of pancreatic digest of casein to papaya digest of soy, respectively) (the remainder being water) was incubated at 37° C. for 20 hours with shaking. The incubated mixture was tested for the presence of aPL, and the result was negative.

Next, IvIg was incubated in a test tube in soy broth, sodium nitroprusside (SNP) and hemin (an iron (ferric) containing protoporphyrin) at 37° C. for 20 hours with shaking. The amounts used were 60 microliters of IvIg, 5 microliters of SNP and 5 microliters of hemin in a total of 1 ml of soy broth. The incubated mixture tested positive for the presence of aPL, particularly aPS (15 MoM) and aPE (41 MoM). (data not shown)

Example 21

A series of experiments was conducted to determine if incubation with hemin alone would be sufficient to cause the appearance of autoantibodies in IvIg or in plasma or serum.

Reconstituted lyophilized IvIg (at a concentration of 100 mg/ml) was added to and incubated in a phosphate buffered saline (PBS) solution with hemin for 20 hours at 37° C. The amounts used were 300 µl of IvIg solution and 5 µl of a hemin solution (75 µg) in a total volume 1 ml.

As shown in FIG. 21, the incubated mixture showed significant amounts of aPS and aPE IgG, and, to a lesser extent, aCL IgG.

When serum or plasma were incubated with hemin under similar conditions, no autoantibodies were detected.

Example 22

The fact that positive results for the presence of autoantibodies could be obtained when IvIg was incubated with hemin, whereas negative results were obtained when serum or plasma were incubated with hemin suggested that serum or plasma could contain substances that inhibit or interfere with the process of obtaining autoantibodies.

Figure 22:
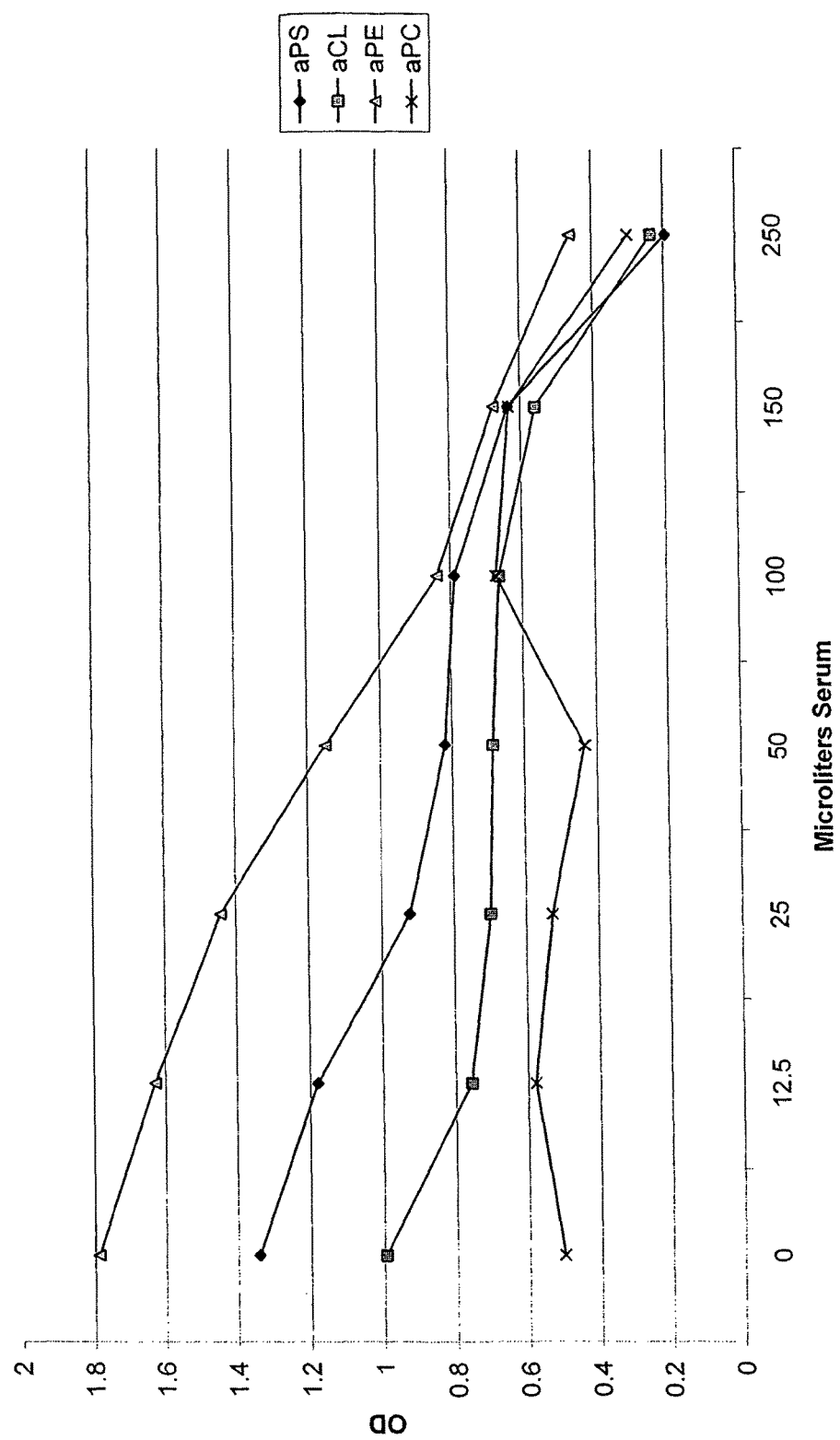
FIG. 22 is a graph showing the amount of aPS, aCL, aPE, and aPC (as measured by optical density, OD) detected in a series of Ivig preparations that were incubated with hemin, as a function of the amount of human serum (in µl) added to the preparations.

In a series of experiments, IvIg was incubated in a Tris buffer with hemin, for 20 hours at 37° C., similar to the process of Example 21, with the added feature that an increasing amount of human serum (the inventor's) was added to the batches before incubation. Each separate batch was tested for the presence of aPS, aCL, aPE and aPC autoantibodies, and the results are shown in FIG. 22. The results shown in FIG. 22 demonstrate that increasing amounts of serum did have an inhibitory effect on the release of antiphospholipid antibodies. Similar results were shown with substituting plasma for serum (data not shown). A possible explanation for these results is that hemin, which contains an iron molecule in the ferric state and which is known as an active oxidizing agent, may act to oxidize a binding site of certain immunoglobulin molecules so that the altered binding site is able to bind self antigens. This process may be inhibited by substances, perhaps antioxidants, in the blood.

Example 23

Figure 23:
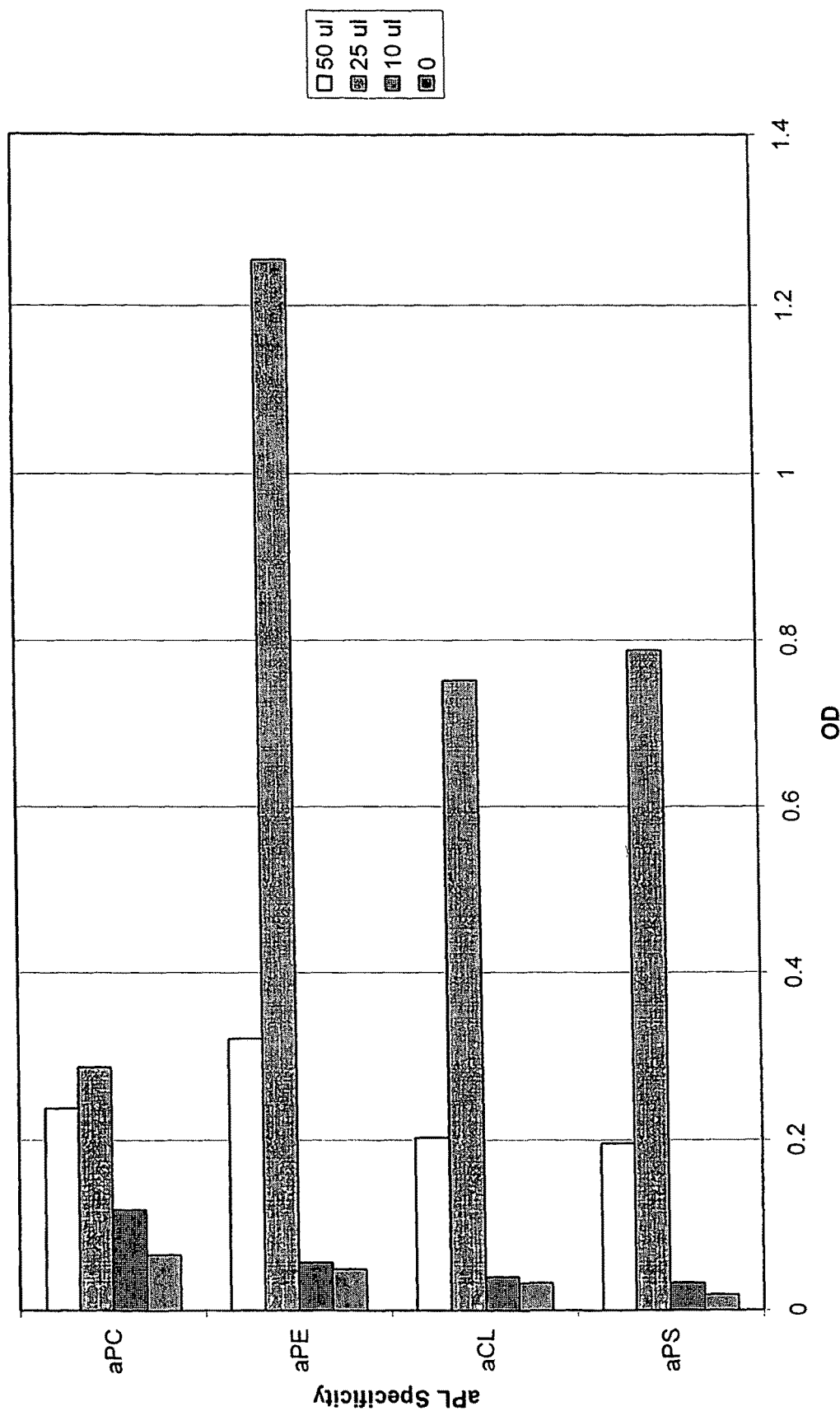
FIG. 23 is a graph showing the amount of aPS, aCL, aPE, and aPC (as measured by optical density, OD) detected in a series of diluted human serum preparations that were incubated with hemin, as a function of the amount of hemin (in µl) added to the preparations.

Human serum (the inventor's) was diluted 1/10 in Tris buffer. In a series of experiments, this diluted serum, in 1 ml batches, was incubated with an increasing amounts of hemin, specifically, 0 µl, 10 µl, 25 µl and 50 µl. (Previously, it had been found that hemin by itself was not sufficient to cause the release of autoantibodies from blood or serum, although it was sufficient to cause such release from IvIg. Therefore, the purpose of diluting the serum was to dilute the effect of any interfering substances found in the blood, such as antioxidants.) The batches were tested for the presence of aPS, aCL, aPE and aPC autoantibodies, and the results are shown in FIG. 23. The results shown in FIG. 23 show that while no significant amounts of autoantibodies were detected in diluted serum when 0 or 10 µl of hemin is added, significant amounts are detected with 25 µl of hemin. For an unknown reason, the amounts of detected autoantibodies were less with 50 µl of hemin.

Example 24

Figure 24:
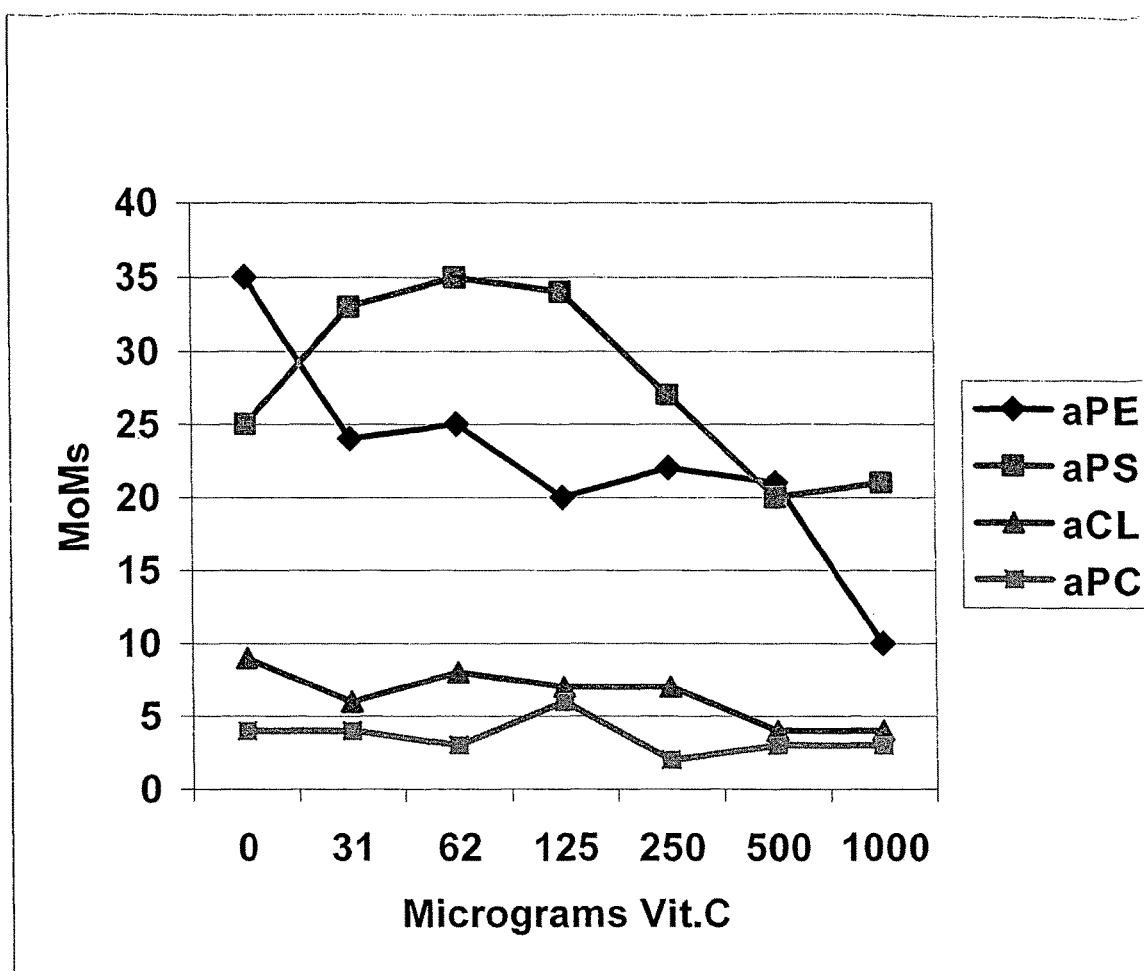
FIG. 24 is a graph showing the amount of aPS, aCL, aPE, and aPC (as measured by multiples of the mean, MoMs) detected in a series of IvIg preparations that were incubated with hemin and Vitamin C, as a function of the amount of Vitamin C (in µg) added to the preparations.

The next series of experiments was designed to determine if an antioxidant such as vitamin C, which is present in blood, would inhibit the release of autoantibodies. In a series of experiments, IvIg was incubated in a Tris buffer with hemin, with the added feature that an increasing amount of ascorbic acid (Vitamin C) was added to the hemin-containing buffer and allowed to mix for 30 minutes before adding the IvIg and before incubation. As shown in FIG. 24, there was about 78% inhibition of hemin-induced aPE release with 1 mg of Vitamin C, an amount that represents a physiological concentration of Vitamin C. There is a biphasic curve with aPS release, which raises the possibility that Vitamin C at low concentrations can act as an oxidizing agent, but becomes an antioxidant (reducing) agent at higher concentrations.

Example 25

Figure 25:
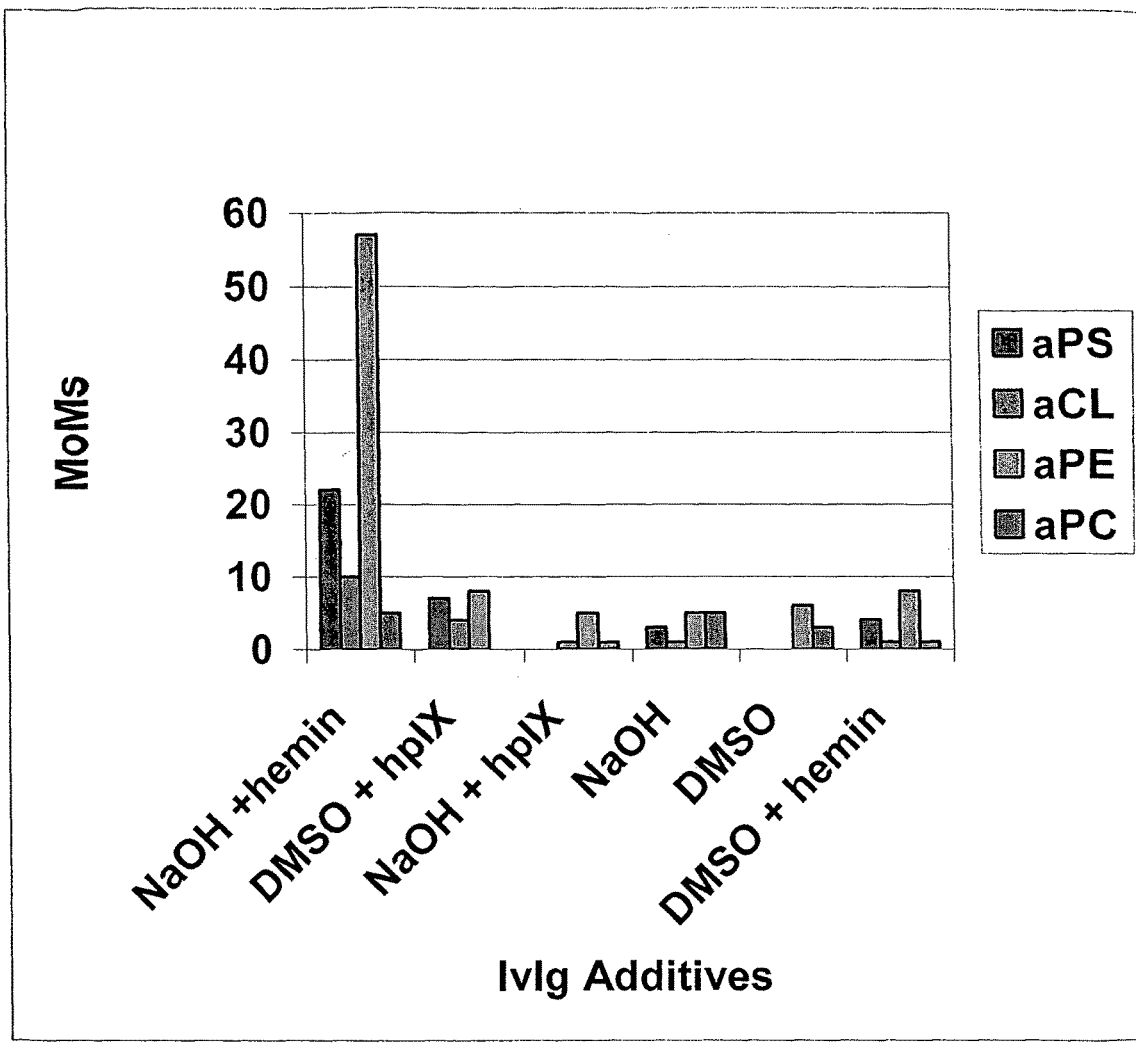
FIG. 25 is a graph showing the amount of aPS, aCL, aPE, and aPC (as measured by multiples of the mean, MoMs) detected in a series of IvIg preparations that were incubated with NaOH solubilized hemin, DMSO-solubilized hematoporphyrin IX (hpIX), NaOH-solubilized hpIX, NaOH alone, DMSO alone, and DMSO-solubilized hemin.

The next series of experiments was designed to determine whether the vehicle that hemin is dissolved in has an impact on the results obtained and whether the iron atom in hemin is necessary. In a series of experiments, IvIg was incubated in a Tris buffer with hemin, or with other additives. In particular, in one instance, hemin was solubilized with NaOH. In another instance, it was solubilized with DMSO. In other instances, hematoporphyrin IX (hpIX), which is the same molecule as hemin, but without the iron (Fe+++), was used in place of hemin and was solubilized with NaOH or DMSO. In other instances, NaOH and DMSO were tested as controls (without hemin or hpIX). As shown in FIG. 25, the use of NaOH solubilized hemin produced positive results for the presence of autoantibodies, whereas hemin+DMSO, hpIX+NaOH, hpIX+DMSO, NaOH alone, and DMSO alone did not produce positive results.

Example 26

Figure 26:
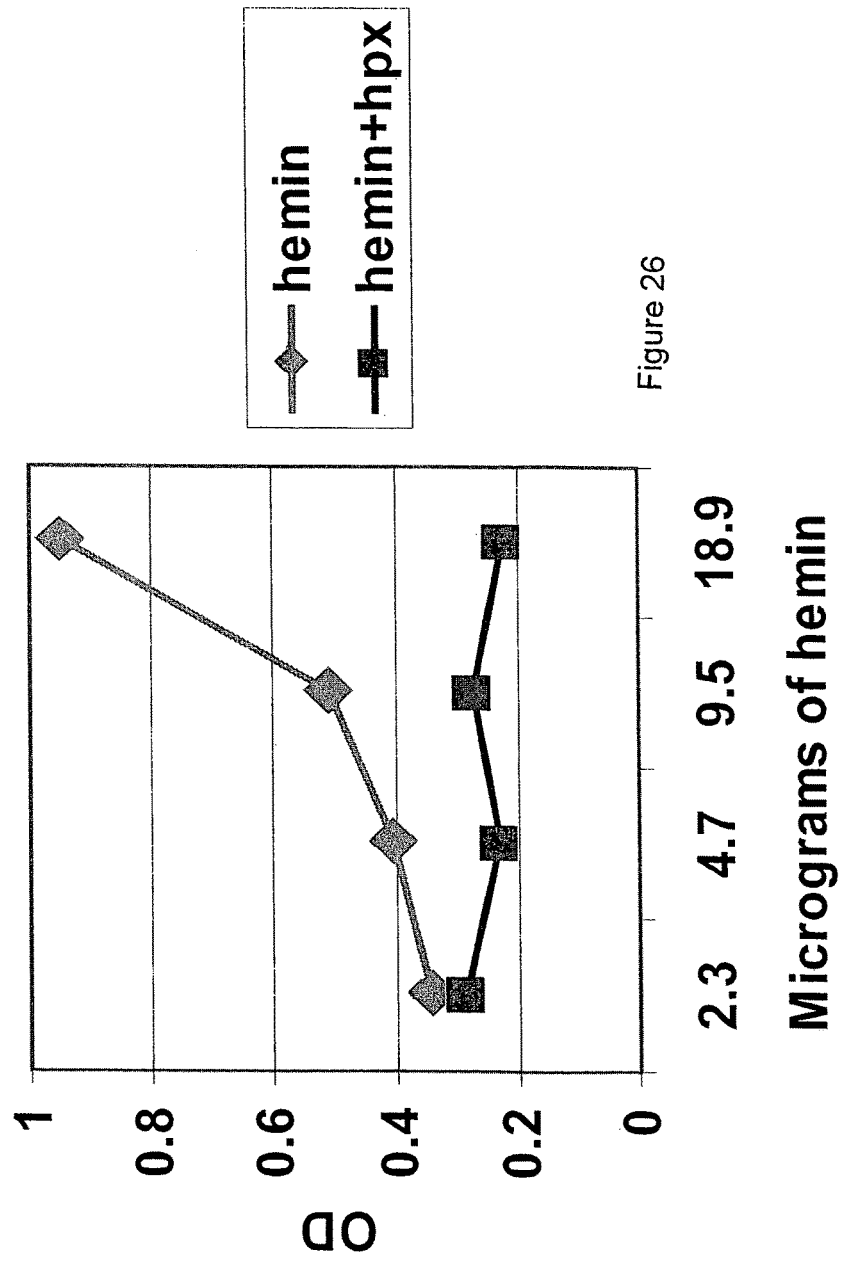
FIG. 26 is a graph showing the amount of aPS (as measured by optical density, OD) detected in a series of Ivig preparations that were incubated with increasing amounts of hemin and increasing amounts of hemin and hemopexin (hpx).

To further establish that hemin was causing oxidation of antibodies, equimolar amounts of hemopexin (Hpx) were added to the IvIg PBS hemin mixture. Hpx is an antioxidant molecule with an extraordinarily high binding affinity for heme iron. Lyophilized Hpx purchased from SciPac (Kent, England) was reconstituted in PBS at 10 mg/ml. Shown in FIG. 26 are the aPS redox data resulting from adding increasing concentrations of hemin to the IvIgG countered with adding equamolar concentrations of Hpx. Because there is an 1:1 binding interaction between hemin and Hpx, the Hpx was able to negate the redox capability of the ferric iron present in hemin.

Example 27

To illustrate the broad range and activity of autoantibodies that can be obtained by an oxidation treatment of IvIg, a series of Western blots were set up using cell lysates from 3 different cell lines using hemin-treated IvIg or untreated IvIg as primary antibodies and using anti-human HRP-tagged conjugate as a control (HRP=horseradish peroxidase). The blots are shown in FIG. 27. The "B" lysate is a B lymphocyte cell line called Raja from a patient with a lymphoma. The "T" lysate is a T-lymphocyte-derived cell line called Jurkat again from a leukemic patient. The U87MG lysate is a glioblastoma blast cell line (brain cancer). The reduced lysates were run into the gel at 50 mg/ml concentration. To obtain the hemin-treated IvIg preparation, 75 µg of hemin was combined with 1 ml of PBS containing 6 mg of IvIgG. Incubation was for 20 hours at 37 degrees. In FIG. 27, the blot wherein hemin-treated IvIg was used as the primary antibodies is labeled "Test IgG; the blot wherein untreated IvIg was used as the primary antibodies is labeled "Control", and the blot to which anti-human HRP-tagged conjugate was applied without primary antibodies is labeled "Secondary". The hemin-treated and untreated IgG preparations were diluted 1/1000 respectively. The anti-human HRP-tagged conjugate was used at a dilution of 1/5000.

These data clearly show that the hemin-treated IvIg has abundant activity towards human cellular components in comparison to untreated IvIgG and the conjugate control, which do not.

Example 28

The next experiment was carried out to determine whether oxidizing agents other than hemin, and in particular, oxidizing agents that do not contain iron, would be effective to unmask autoantibodies. A mixture of 25 µg of potassium permanganate ($KMnO_4$) at a concentration of 100 µM, and 2 mg of IvIg in a total volume of 1 ml of phosphate buffered saline was incubated overnight at 37° C. In the incubated mixture, aPC and aPS could be detected. aCL was usually detected, but not aPE (data not shown). It was later determined that a reason why aPE is not detected is because $KMnO_4$ alters the PE phospholipid antigen used in the ELISA testing.

Example 29

After it was shown that autoantibodies could be unmasked by oxidation reactions, the next question was whether electrochemical methods, such as an electromotive force from a battery, could achieve the same effect.

IvIg was dissolved in a phosphate buffered saline solution, and, in separate experiments, galvanized steel, copper, or stainless steel electrodes were connected to the positive and negative terminals of a 9-volt battery and were submersed into the solution for 1-2 minutes. During this period, bubbling was noticed in the solution and the PBS solution changed color (blue when copper wires were used, brown when stainless steel wires were used and green when galvanized steel wires were used). As shown in FIGS. 28A and 28B, the treated solution tested positive for the presence of aPS, aCL, aPE and aPC autoantibodies, in aPL dependent testing, and positive for the presence of aPS, aPE and aPC autoantibodies in aPL independent testing.

Example 30

To avoid the interaction of metals with the solution and thereby determine the effect only of an electric current, graphite electrodes were used in place of the metal electrodes. Graphite is inert, but is able to pass electrons into conducting solutions without participating in reactions.

Figure 29:
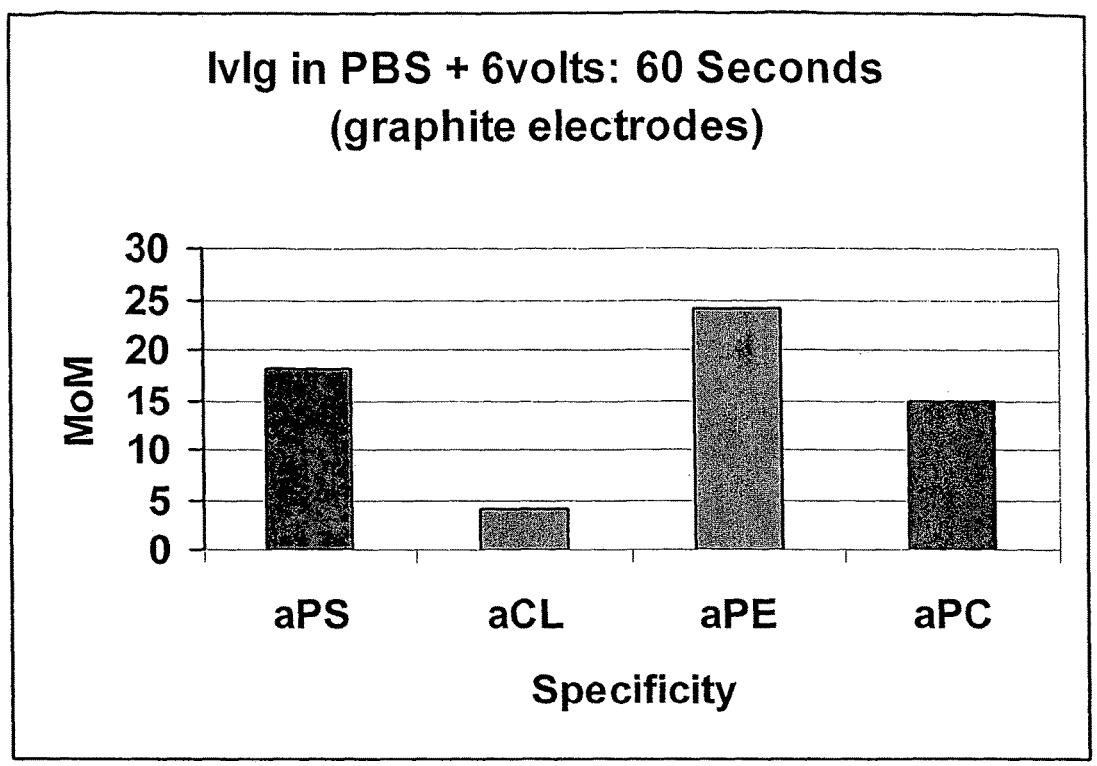
FIG. 29 is a graph showing the amount of aPS, aCL, aPE, and aPC (as measured by multiples of the mean, MoMs) detected in a series of IvIg preparations in which electrodes connected to a 6 volt battery were immersed in a phosphate buffered saline solution containing the IvIg for 60 seconds.

IvIg was dissolved in a phosphate buffered saline solution, and graphite electrodes connected to the positive and negative terminals of a 6-volt battery were submersed into the solution for 60 seconds. As shown in FIG. 29, the treated solution tested positive for the presence of aPS, aPE and aPC autoantibodies.

Example 31

In the experiments involving applying electric current to solutions of IvIg in phosphate buffered saline, a significant increase in pH was noticed, possibly due to the formation of NaOH. In order to keep the reactions at physiological pH levels, a cell culture medium, RMPI, was substituted for the phosphate buffered saline.

Figure 30:
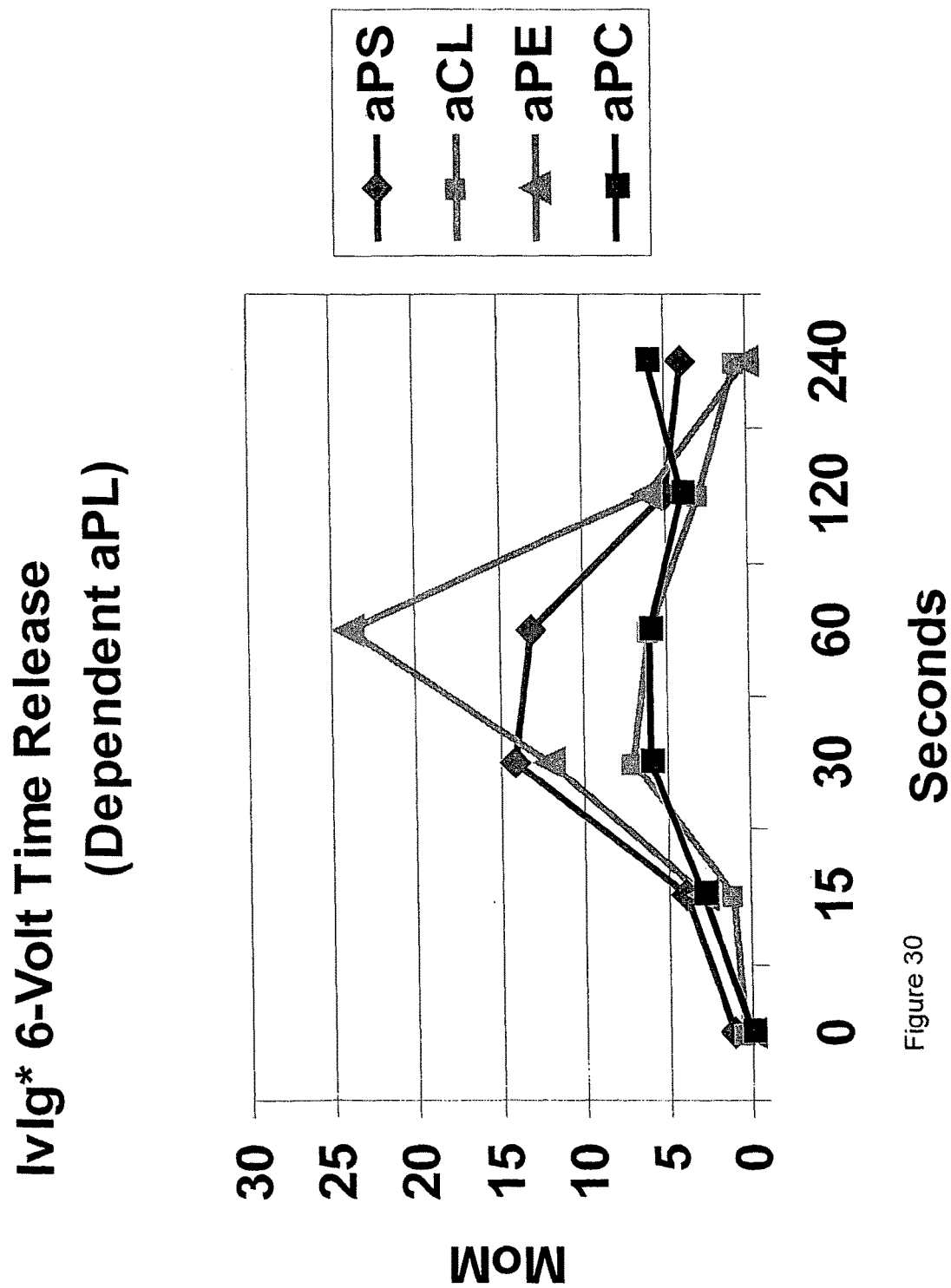
FIG. 30 is a graph showing the amount of aPS, aCL, aPE, and aPC (as measured by multiples of the mean, MoMs) detected in a series of IvIg preparations in which electrodes connected to a 6 volt battery were immersed in a phosphate buffered saline solution containing the IvIg, as a function of the time of immersion.

The next series of experiments was carried out to determine the effects of the time of exposure to the electric current on the unmasking of autoantibodies. IvIg was dissolved in RMPI, a cell culture medium and graphite electrodes connected to the positive and negative terminals of a 6-volt battery were submersed into the solution for a variable amount of time. As shown in FIG. 30, the maximum release of dependent aPL was obtained after 60 seconds of exposure to the current. Curiously, between 2 minutes and 4 minutes, the amount of aPL declined or disappeared.

Example 32

Since the previous experiment had shown that aPL antibodies could be obtained from IvIg after exposure to an electric current, but that the aPL antibodies disappeared after further exposure to the current, the next question was whether the unmasking of autoantibodies could be reversed by an electric current. That is, could a positive control serum be treated so that autoantibodies were no longer detectable?

Figure 31A:
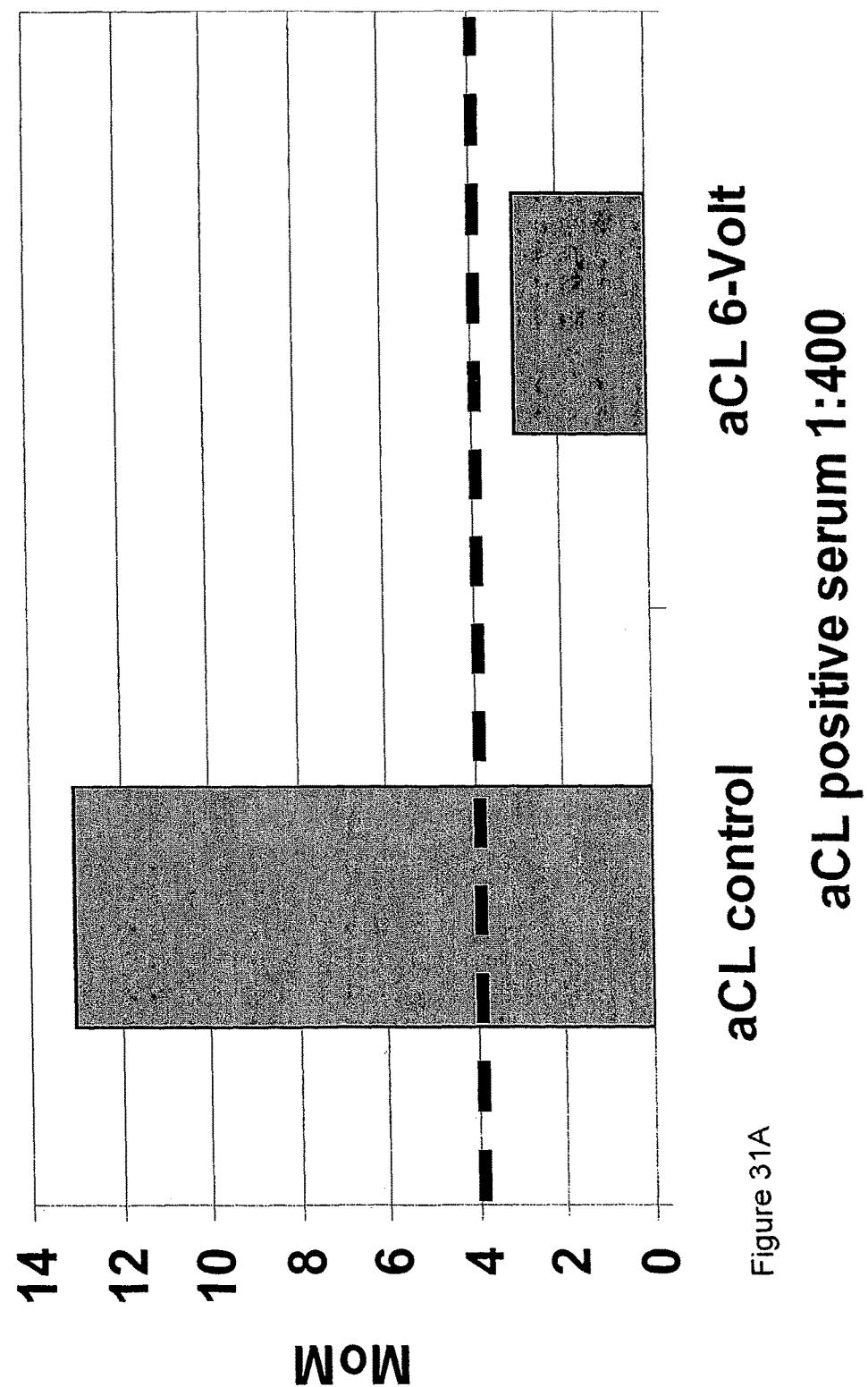
FIGS. 31A, 31B and 31C are graphs showing the amount of aCL, aPE, and aPS, respectively (as measured by multiples of the mean, MoMs), detected in control solutions before and after exposure for 240 seconds to electrodes connected to a 6 volt battery.
Figure 31B:
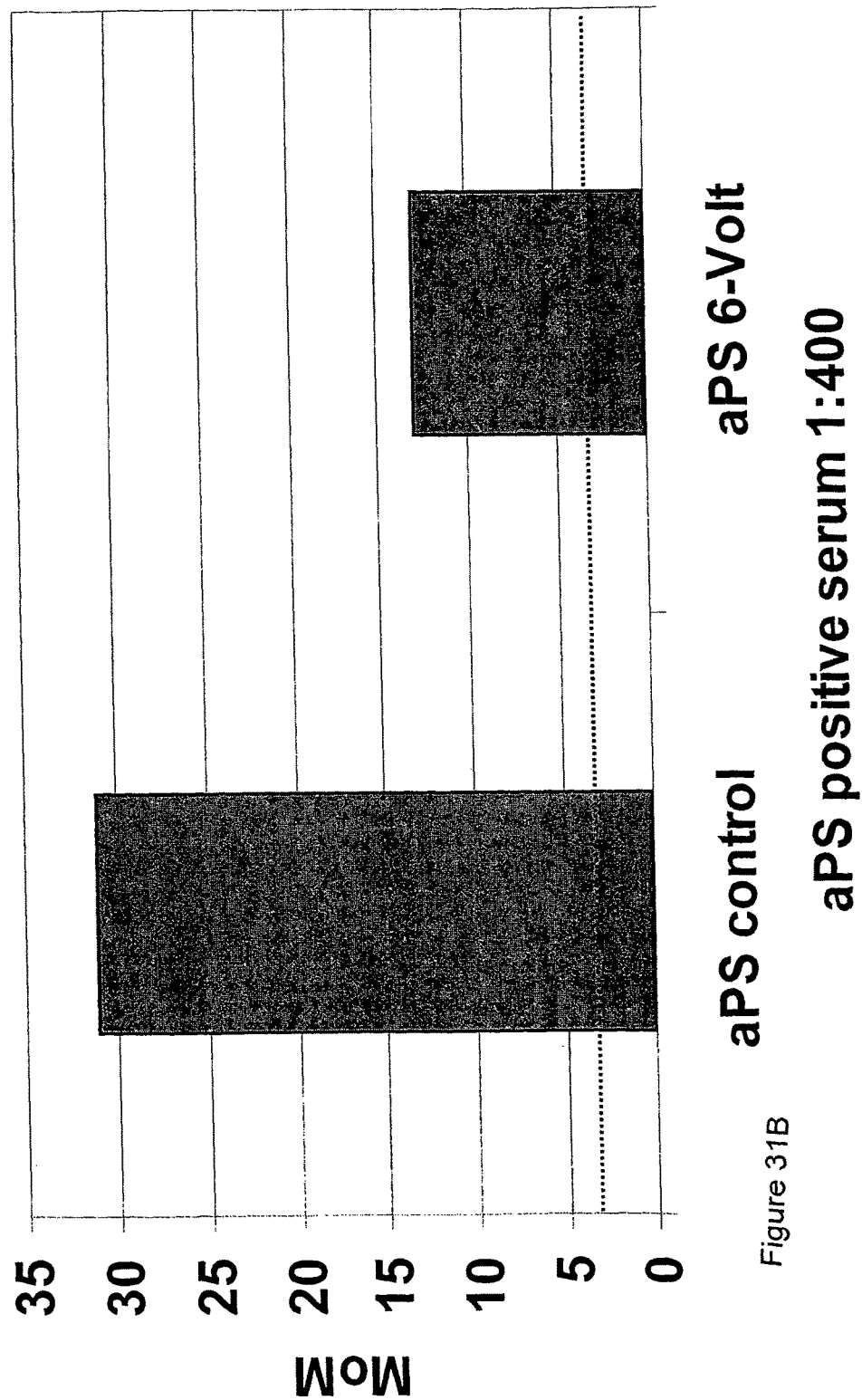
Figure 31C:
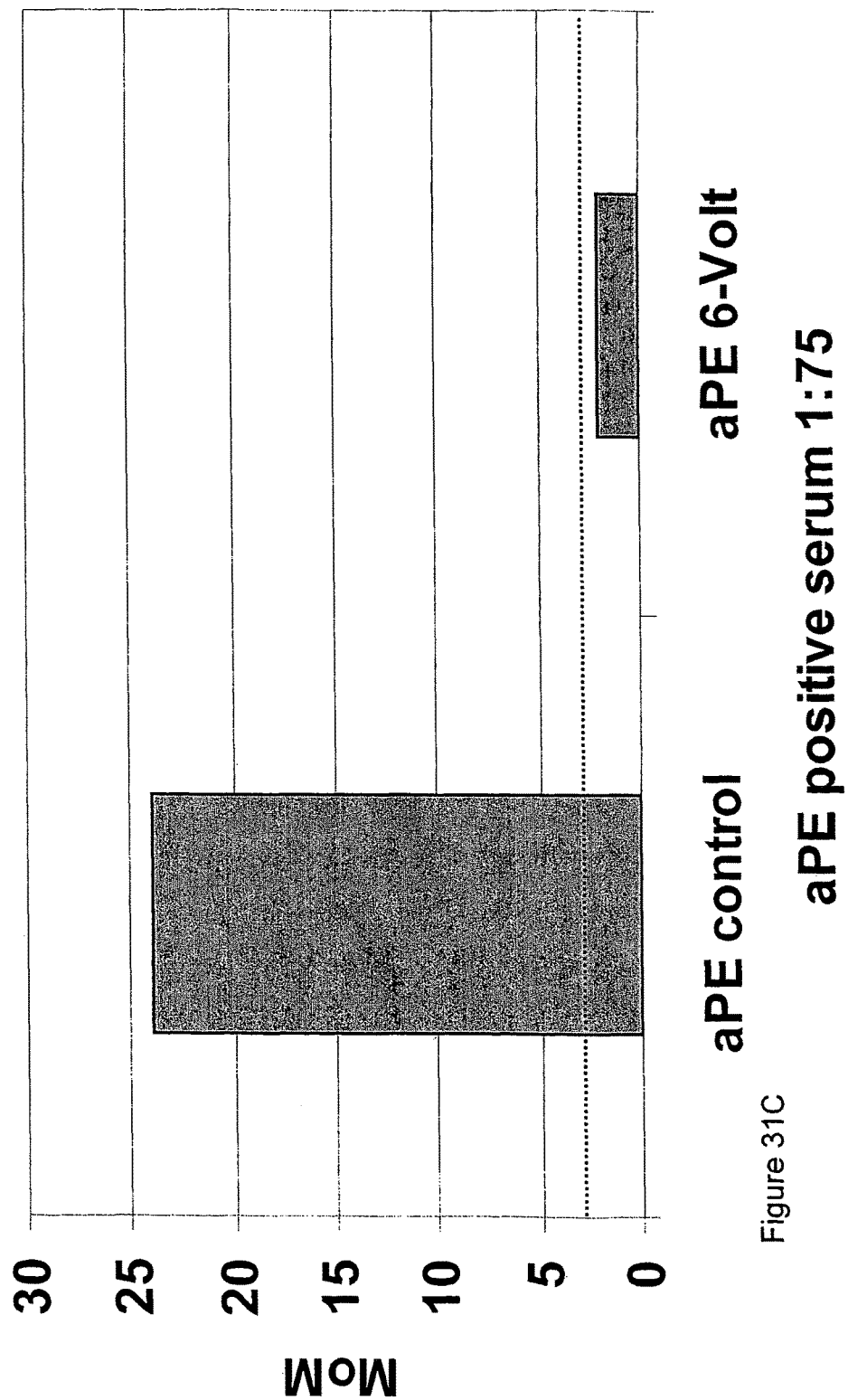

In separate experiments, aCL positive control serum, at a dilution of 1:400, aPE positive control serum at a dilution of 1:75, and aPS at a dilution of 1:400 were exposed to an electric current by immersing graphite electrodes connected to the positive and negative terminals of a 6-volt battery for up to 240 seconds. As shown in FIGS. 31A-31C, each control sera became negative for its respective specificity.

Example 33

Figure 32:
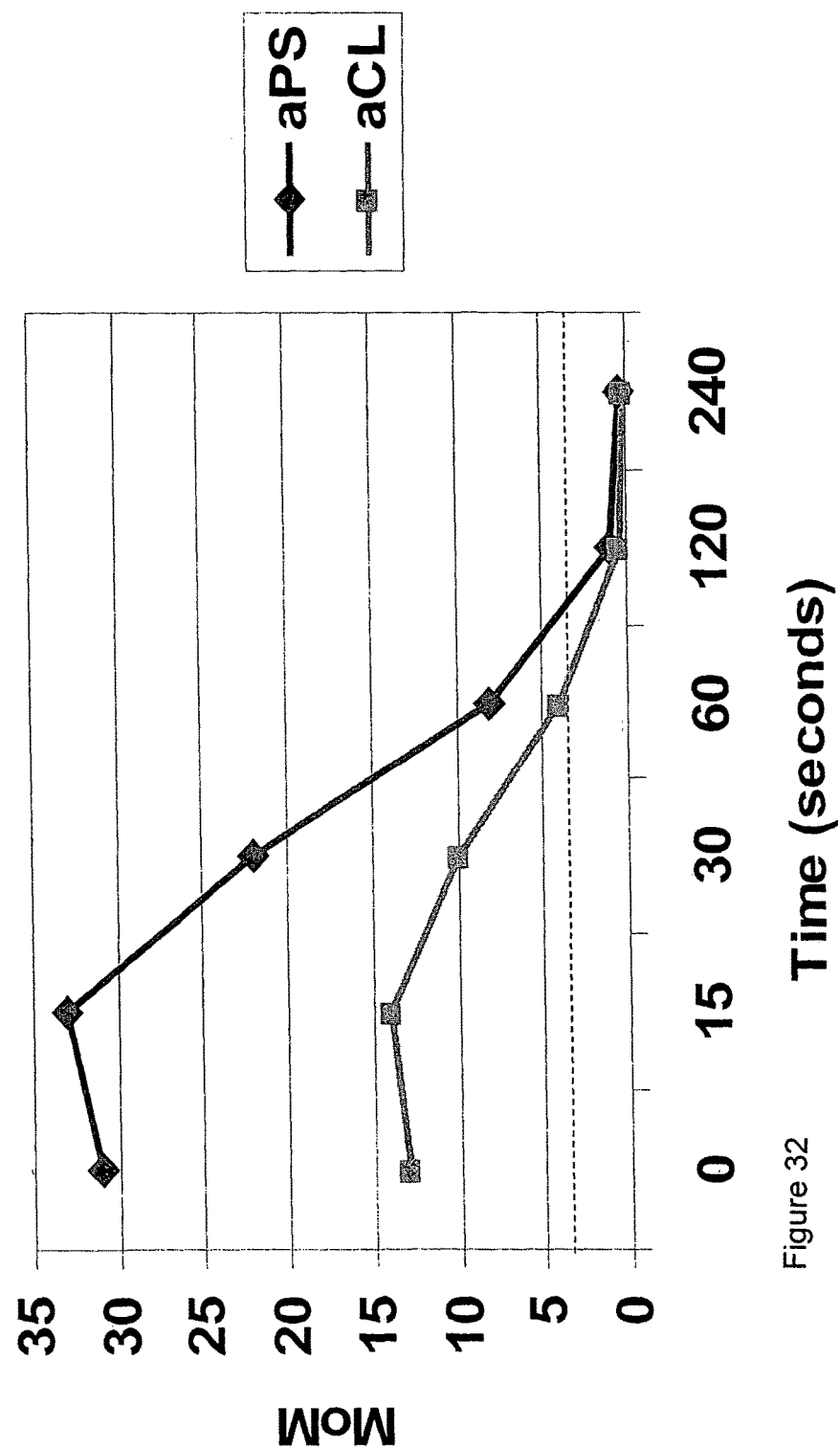
FIG. 32 is a graph showing the amount of aPS and aCL, respectively (as measured by multiples of the mean, MoMs), detected in the PBS-diluted serum of an aPS and aCL-positive-patient. In the experiment, graphite electrodes connected to a 6 volt battery were immersed in the diluted serum for a variable amount of time.

Based on the results in Example 32, the next question that was asked was whether autoantibodies of a patient having an autoimmune disease could be remasked if the patient serum was exposed to an electric current. Serum from a patient having elevated levels of aPS and aCL was diluted 1/400 with phosphate-buffered saline (the dilution in PBS was in an amount that would achieve an OD value of 1.000 in 10-15 minutes) and graphite electrodes connected to the positive and negative terminals of a 6-volt battery were submersed into the solution for a variable amount of time. As shown in FIG. 32, the amount of aCL and aPS detectable in the samples of the autoimmune patient's serum declined significantly after 30 seconds and was no longer detectable after 2 minutes. These experiments were repeated for other patients' antibodies and the same result was obtained (data not shown).

Example 34

In an early experiment, a blood sample from a patient who had a very specific and high titer IgA aPE was exposed to hemin in a routine microbiology culture bottle. It was observed that after exposure to hemin her IgA aPE disappeared, and the emergence of IgG aPS, aCL and most spectacularly, IgG aPE was detected in the aPL ELISA. At the time, an explanation for this phenomenon was not readily apparent.

Figure 33:
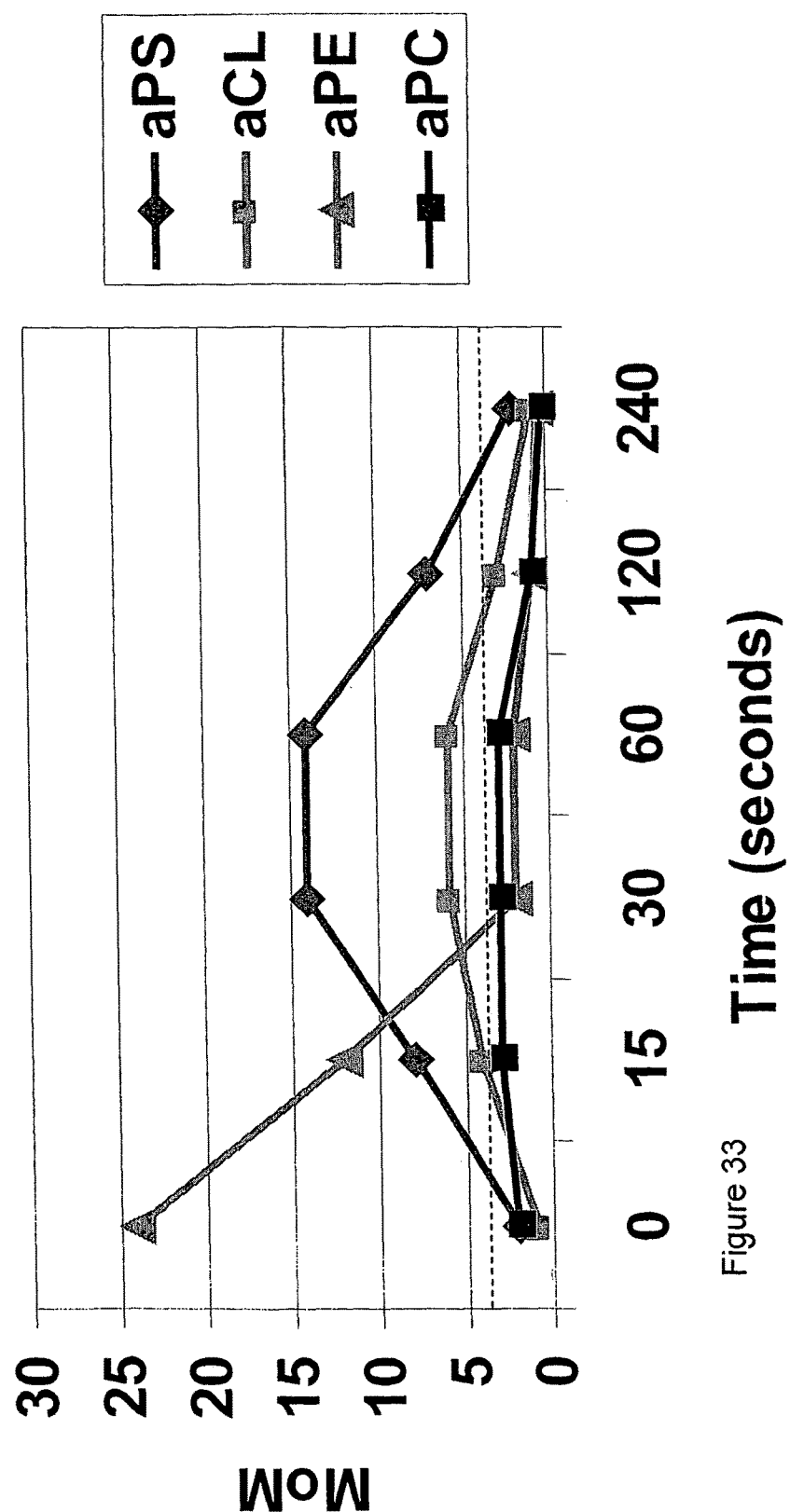
FIG. 33 is a graph showing the amount of aPS, aCL, aPE, and aPC (as measured by multiples of the mean, MoMs), respectively, detected in the PBS-diluted serum of an aPE-positive patient. In the experiment, graphite electrodes connected to a 6-volt battery were immersed in the diluted serum for a variable amount of time.

With the discovery of a faster unmasking process using electric current, it became possible to confirm the earlier results with another patient having a high aPE. In this experiment, serum from a patient having a high aPE was diluted in PBS by 1/75 and graphite electrodes connected to the positive and negative terminals of a 6-volt battery were submersed into the solution for a variable amount of time. As shown in FIG. 33, the aPE became undetectable (masked) within 30 seconds of a 6-volt DC current application, with a concomitant unmasking and detection of aPS and aCL IgG. The newly unmasked aPL peaked around 30 seconds only to become masked again after 2-4 minutes of exposure.

An important technical aspect addressed by the above experiment was that the patient aPE was treated apart from the plasma protein diluent used in the assay, in the present case, 10% adult bovine plasma (ABP). In other experiments not shown, the diluted patient sera were exposed to 6-volt EMF conditions before adding the plasma proteins used in the ELISA diluent. The important aspect of these experiments was to show that the EMF effects were being applied to the patients' antibodies and not to EMF changes in the plasma proteins used in the diluent.

These experimental data support the observations that redox reactions are determining the appearance and disappearance of different antibody specificities. What is also learned from these experiments is that the redox effects appear to be limited to the antibody binding site(s), the Fab portion of the antibody molecule. This is because the heterologous antihuman antibody-labeled conjugates used in the ELISA are not affected as the conjugates continue to recognize the different antibody heavy chain targets (Fc portions) of the antibody molecules. Thus, as the human antibody is not consumed or destroyed by redox, the most plausible explanation is that the antibody-binding site in the Fab portion of the antibody molecule contains accessible electrons that can participate in the oxidation/reduction process.

Example 35

Figure 34:
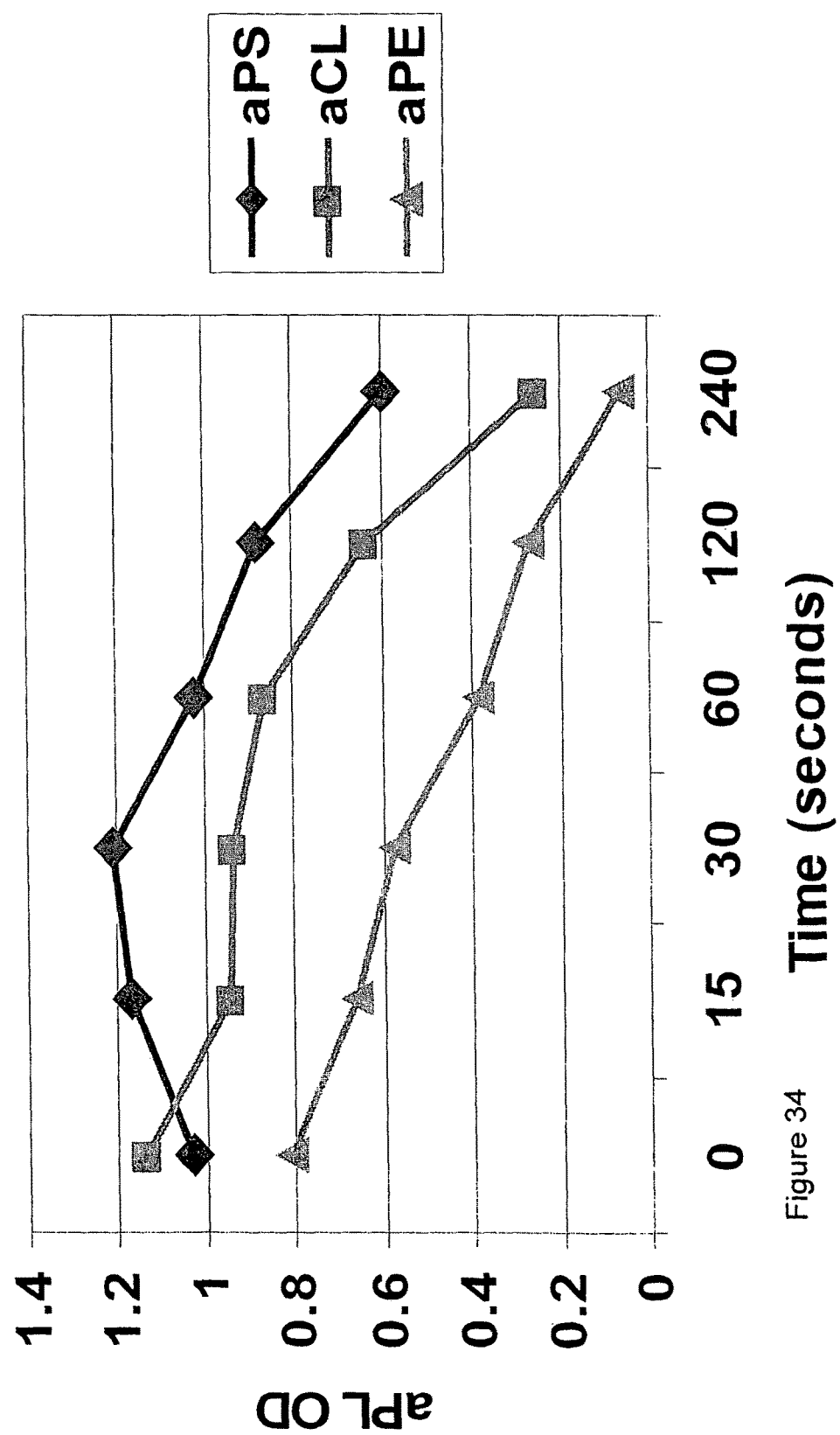
FIG. 34 is a graph showing the amount of aPS, aCL and aPE, (as measured by optical density, OD), respectively, detected in the PBS-diluted serum of an aPE-positive patient. In the experiment, the 10% adult bovine plasma (ABP) used in the determination of protein-dependent aPL binding was treated by immersing graphite electrodes connected to a 6-volt battery in the ABP for a variable amount of time.
Figure 35:
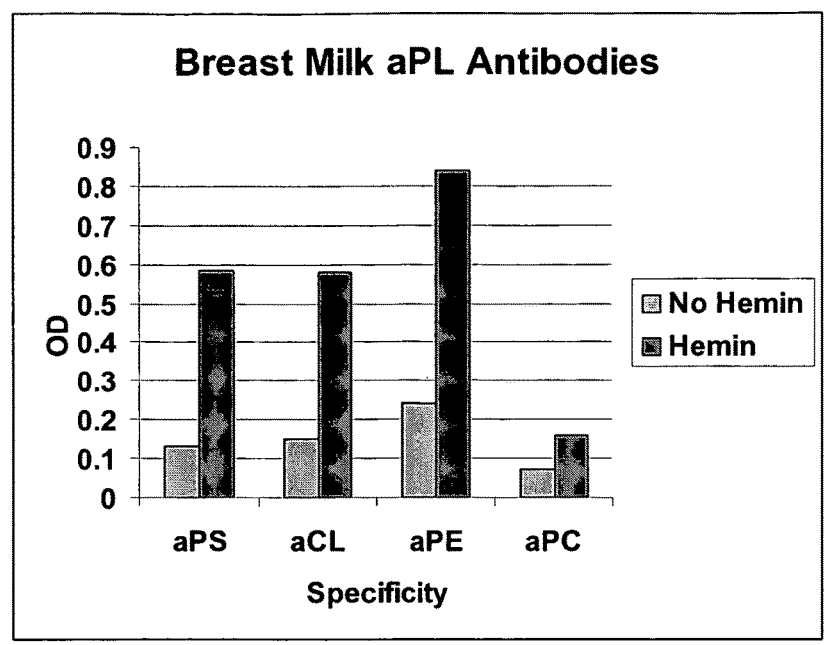
FIG. 35 is a graph comparing the amount of aPS, aCL, aPE, and aPC (as measured by optical density, OD) detected in an unincubated sample of human breast milk with the amount detected in a sample of human breast milk that was incubated with hemin.

The next experiments were carried out to see whether plasma proteins other than autoantibodies can have their binding specificity altered by oxidation-reduction. In these experiments, a 10% adult bovine plasma (ABP) solution, the same solution containing phospholipid-binding proteins that had been used to determine protein-dependent aPL binding, was exposed to an electric current from a 6-volt battery for a variable period of time. The treated ABP samples were then used in ELISA assays with aPS-, aCL- and aPE-positive patient sera to see if the treatment of the ABP would affect the outcome of the ELISA. As shown in FIG. 34, at time zero (untreated ABP), the positive patient sera give the aPL response in ABP that is routinely seen. As the 10% ABP is exposed to oxidation-reduction (EMF) over time, amount of aPL detected diminishes and after 2 minutes, the aPE positive serum is no longer positive. These results indicate that the plasma proteins that are responsible for the patients' aPL reactivity are altered by the exposure to the electric current. For example, as kininogen is the plasma protein responsible for providing a positive ELISA signal for aPE dependent reactions (the kininogen binds to PE, then the antibody binds to the kininogen, the aPE however will not bind to either PE or kininogen independently), this shows that the kininogen in the ABP sample is being altered by the redox exposure. aCL is also negative at 240 seconds exposure and since this patient serum requires either prothrombin and/or beta2 glycoprotein (or both could be involved) for producing a positive signal in the aPL ELISA, these two proteins must also be altered by the redox reactions. The same two plasma proteins are involved in the aPS example.

Example 35

An experiment was carried out to see whether human breast milk contains autoantibodies. In this experiments, the aPS, aCL, aPE and aPC levels in breast milk taken from a mother of a 5-month old baby were determined before and after treatment with hemin. As shown in FIG. 36, the detected amount of each autoantibody, as determined by OD was dramatically increased in the samples that were treated with hemin. Accordingly, it can be concluded that human breast milk contains masked antibodies. Therefore, the present invention further provides a product comprising non-human milk such as cow or goat milk that is supplemented with masked human antibodies.

Example 36

Figure 36A:
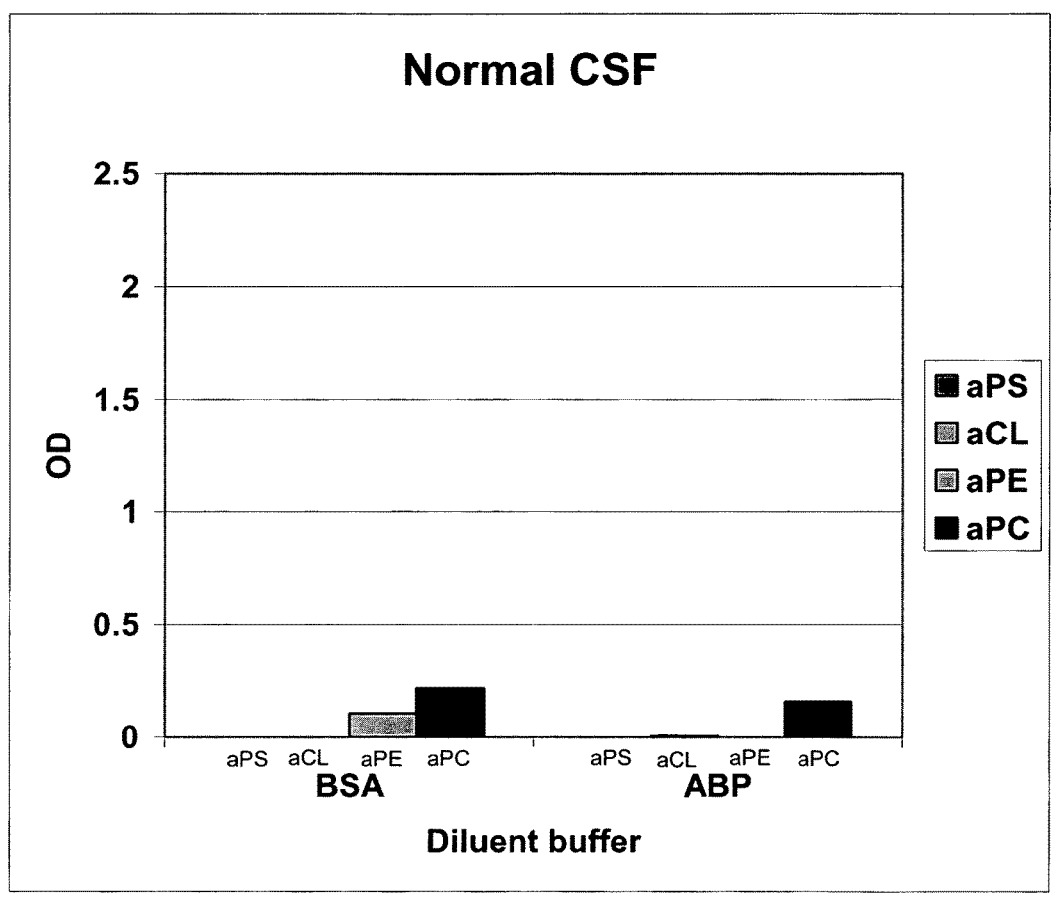
FIGS. 36A and 36B are graphs showing the amount of aPS, aCL and aPE, (as measured by optical density, OD), respectively, detected in the CSF fluid of a normal subject, for both unincubated samples and samples that were incubated with hemin. Results are shown for both PBS-diluted and ABP-diluted samples.
Figure 36B:
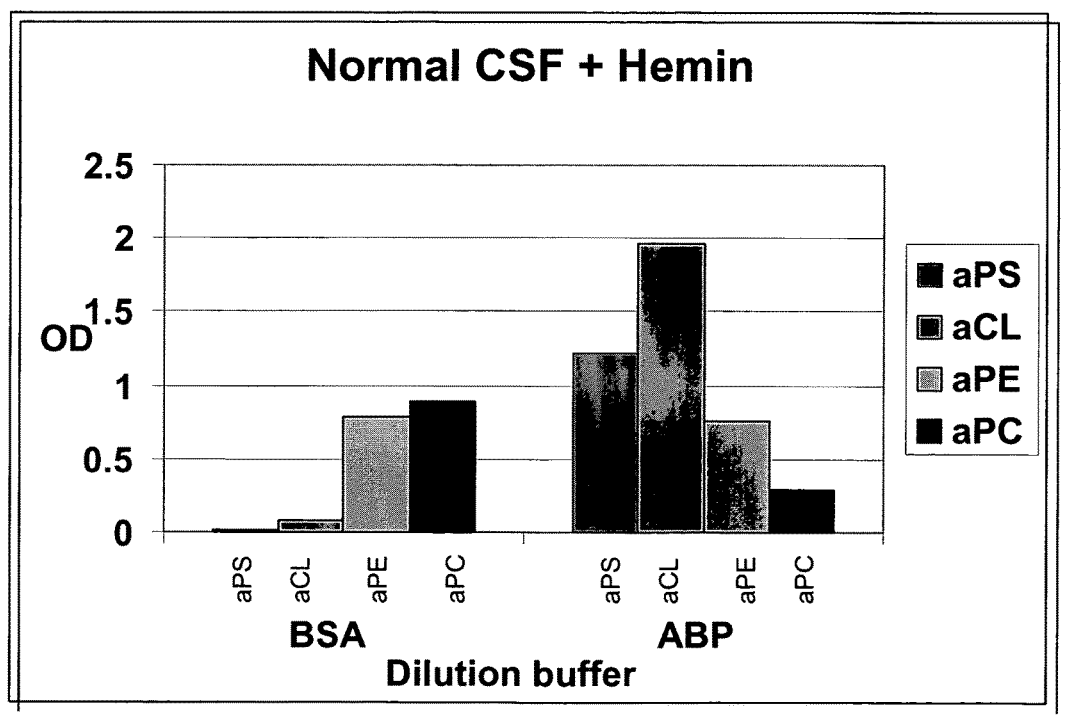

An experiment was carried out to see whether human cerebral spinal fluid contains autoantibodies. In this experiment, spinal fluid was taken by spinal tap from a normal individual and samples in BSA and ABP dilution buffers were assayed for aPS, aCL, aPE and aPC levels before and after treatment with hemin. As shown in FIGS. 36A and 36B, samples showed none or minimal levels of antiphospholipid antibodies before treatment, and substantial increases in the levels after treatment, with aPE and aPC showing the highest levels in a BSA buffer and aPS and aCL showing the highest levels in the ABP buffer.

Example 37

Figure 37:
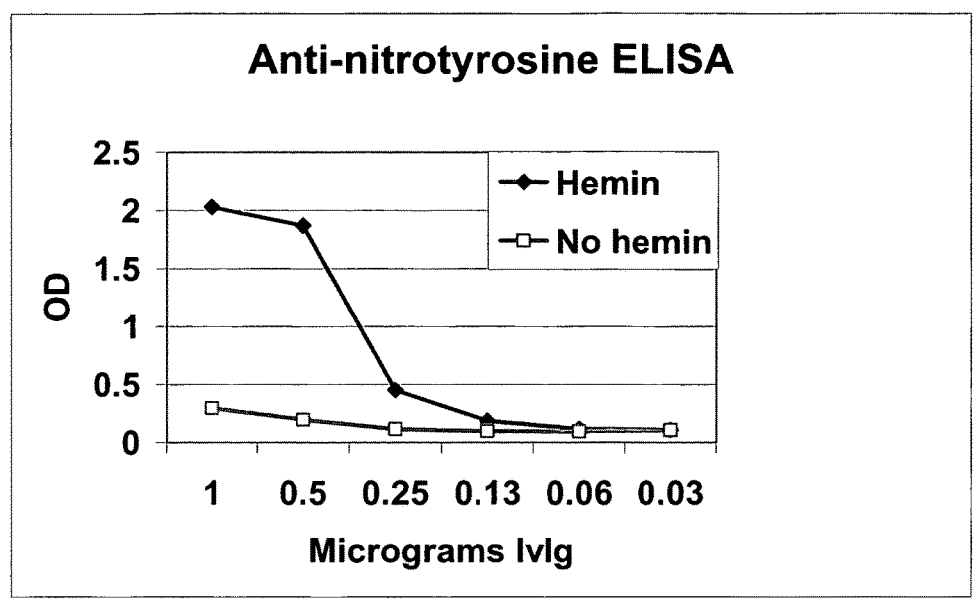
FIG. 37 is a graph comparing the amount of IgG detectable by monoclonal anti-nitrotyrosine in an IgG sample that has been treated with hemin and an IgG sample that has not been treated with hemin.

An anti-nitrotyrosine assay was conducted on hemin-treated and control IgG to determine if there was a difference in the amount of nitrotyrosine residues between the hemin-treated and control IgG samples. ELISA plate wells were coated with hemin-treated and control IgG, dried overnight, blocked with 1% BSA, washed and reacted with mouse anti-nitrotyrosine (1/3000, Upstate, USA, clone 1A6). After washing, alkaline phosphatase conjugated goat antimouse IgG (Sigma, St. Louis, Mo.), was added. Additional washing was followed by substrate development for 2 hrs at 37° C. and quantitative determinations. As shown in FIG. 37, considerably greater nitration is shown in the treated IgG. This finding provides support for the theory that the alteration of binding specificity of antibodies according to the method of the present invention is effected by nitrosylation of tyrosine residues at or near the antigen binding site, which may induce conformational changes that affect the binding specificity of the binding site.

Example 38

IvIg was incubated with hemin and was tested for reactivity with neutrophils using flow cytometry and fluorescent conjugated antihuman IgG antibodies. Comparative testing was done with untreated IvIg. FIG. 38A shows anti-neutrophil reactivity without IvIg NHS. FIG. 38B shows the auto-anti-neutrophil activity of untreated IvIg. FIG. 38C shows the auto-anti-neutrophil activity of 1 mg of hemin-treated IvIg and FIG. 38D shows the auto-anti-neutrophil activity of 3 mg of hemin-treated IvIg, showing strong auto-anti-neutrophil activity. Accordingly, it was found that IvIg processed according to the method of this invention releases autoantibodies that specifically target neutrophils, which contain membrane bound peroxidases, especially NADPH oxidase. These results suggest that unmasked antibodies can participate in any reaction that involves a "respiratory burst" and formation of superoxide ions.

Example 39

Figure 39A:
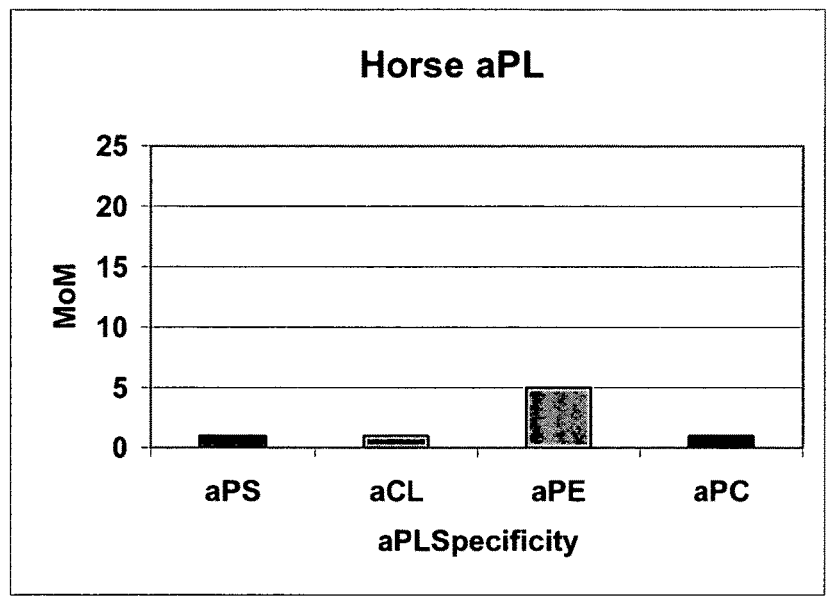
FIGS. 39A and 39B are a graph comparing the amount of aPS, aCL, aPE, and aPC (as measured by optical density, OD) detected in an unincubated sample of horse serum with the amount detected in a sample of horse serum that was incubated with hemin.
Figure 39B:
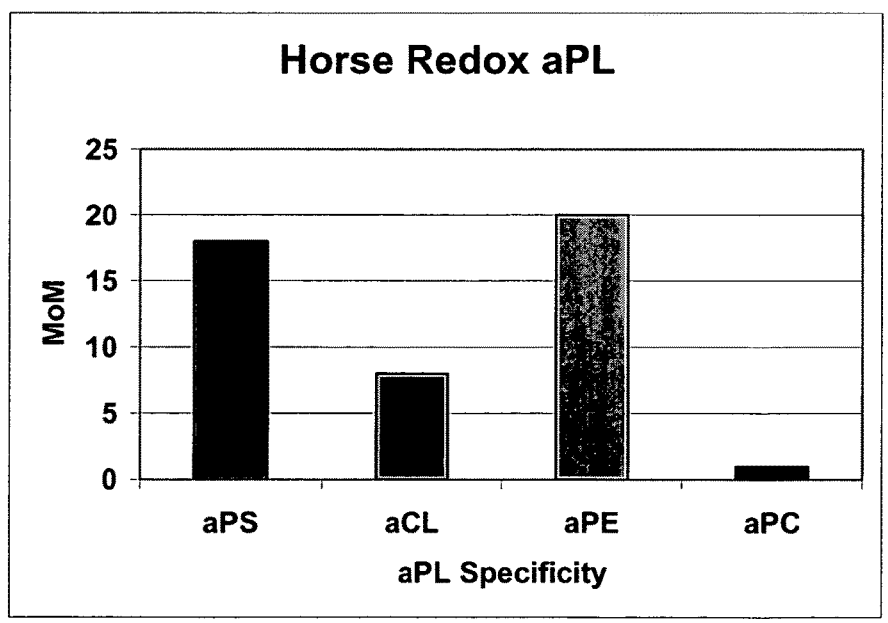

Experiments were carried out to see whether autoantibodies could be detected in other animals. In this experiments, the aPS, aCL, aPE and aPC levels in horse plasma were determined before and after treatment with hemin. As shown in FIGS. 39A and 39B, the detected amount of each autoantibody, as determined by OD was dramatically increased in the samples that were treated with hemin. Accordingly, it can be concluded that horse plasma contains masked antibodies. In similar experiments, autoantibodies of an IgY isotype were detected in chickens (data not shown).

Obviously, many modifications and variations of the present invention are possible in light of the above teachings. It is therefore to be understood that, within the scope of the appended claims, the invention may be practiced otherwise than as specifically described.

We claim:

1. A method comprising the steps of
   providing a composition comprising at least one protein suspended or dissolved in a liquid medium, the protein being selected from the group consisting of immunoglobulins and antibodies and having a binding specificity that can be reversibly altered by a change in its redox state, and
   exposing the composition to an oxidizing agent or a DC current sufficient to reversibly effect the alteration of the binding specificity of said protein, wherein said oxidizing agent is a compound that is capable of altering the redox state of a biological molecule by being reduced and acting as an electron acceptor for other molecules that act as electron donors, said oxidizing agent being at a concentration sufficient to alter the binding specificity of said protein but less than a concentration that would destroy or denature said protein.

2. The method of claim 1 wherein the liquid medium comprises a bodily fluid that naturally contains said protein.

3. The method of claim 2 wherein said bodily fluid is from a vertebrate.

4. The method of claim 2 wherein said bodily fluid is from a mammal or bird.

5. The method of claim 2 wherein said bodily fluid is from a human.

6. The method of claim 2 wherein said bodily fluid comprises diluted whole blood, diluted serum, diluted plasma, raw milk, lymphatic fluid, or CNS fluid.

7. The method of claim 1 wherein the composition the protein is intravenous immunoglobulin (IvIg).

8. The method of claim 1 wherein the protein is an antibody of IgG, IgA, or IgM isotype.

9. The method of claim 1 wherein the protein is an autoantibody of IgG, IgA, or IgM isotype.

10. The method of claim 1 wherein the protein is an antibody.

11. The method of claim 1 wherein the oxidizing agent is a ring compound containing a coordinated metal atom.

12. The method of claim 1 wherein the oxidizing agent is a ring compound containing a coordinated iron atom.

13. The method of claim 1 wherein the oxidizing agent is hemin.

14. The method of claim 1 wherein the oxidizing agent is $KMnO_4$.

15. The method of claim 1 wherein the oxidizing agent is chlorophyll.

16. The method of claim 1 wherein the protein contains at least one tyrosine residue at an antigen binding site of the protein and wherein the oxidizing agent or electric potential alters the binding specificity of the protein by promoting a reversible tyrosine nitrosylation of at least one tyrosine residue at the antigen binding site.

17. The method of claim 1 wherein the binding specificity of the protein altered from a status wherein the protein does not have binding capability with respect to a specific antigen to a status wherein the protein has a binding capability with respect to the specific antigen.

18. A method comprising the steps of
   providing a composition comprising a biological fluid or extract of a biological fluid, wherein the biological fluid or extract contains at least masked protein selected from the group consisting of immunoglobulins and antibodies and having a binding site with a binding specificity that can be altered by participation in a redox reaction,
   exposing the composition to an oxidizing agent or a DC current sufficient to effect the alteration of the binding specificity of said masked protein, thereby unmasking the protein, wherein said oxidizing agent is a compound that is capable of altering the redox state of a biological molecule by being reduced and acting as an electron acceptor for other molecules that act as electron donors, said oxidizing agent being at a concentration sufficient to alter the binding specificity of said masked protein but less than a concentration that would destroy or denature said masked protein, and
   detecting the unmasked protein in the composition and/or recovering the unmasked protein from the composition.

19. The method of claim 18 wherein said biological fluid is diluted whole blood, diluted serum, diluted plasma, diluted placental cord blood, milk, lymphatic fluid or CNS fluid.

20. The method of claim 18 wherein the biological fluid is diluted whole blood, serum or plasma that is pooled from a plurality of subjects.

21. The method of claim 18 wherein the masked protein is an antibody.

22. The method of claim 18 wherein the masked protein is an IgA autoantibody and the biological fluid is mammalian milk.

23. The method of claim 18 wherein the masked protein is an IgG autoantibody and the wherein the biological fluid is CNS fluid.

24. The method of claim 18 wherein the masked protein is selected from the group consisting of
an antibody specific for glutamic acid decarboxylase (GAD);
an antibody specific for tyrosine phosphatase (IA-2);
an anti-lupus anticoagulant antibody;
an anti-phospholipid antibody;
an antinuclear antibody (ANA);
an anti-lamin antibody;
an anti-nucleolus antibody;
an anti-nuclear membrane antibody;
an anti-mitochondria antibody;
an anti-Golgi antibody;
an anti-granulocyte antibody;
an anti-neutrophil antibody;
an anti-monocyte antibody;
an anti-B lymphocyte antibody;
an anti-myeloperoxidase antibody;
an anti-tumor cell antibody;
an anti-trophoblast antibody;
an anti-HLA antibody;
an anti-factor VIII antibody;
an anti-platelet factor 4/heparin complex antibody; and
an anti-beta2-glycoprotein I antibody.

25. The method of claim 18 wherein the masked protein is selected from the group consisting of anticardiolipin, antiphosphatidylcholine, antiphosphatidylethanolamine and antiphosphatidylserine.

26. The method of claim 18 wherein the masked protein contains at least one tyrosine residue at an antigen binding site of the protein and wherein the oxidizing agent or electric potential alters the binding specificity of the protein by promoting a reversible tyrosine nitrosylation of at least one tyrosine residue at the antigen binding site.

27. A method of detecting and/or obtaining and isolating an autoantibody from an antibody-containing biological fluid or from an antibody-containing extract of a biological fluid, said biological fluid or extract containing autoantibodies that, before the method is carried out, are not capable of binding to an antigen and therefore are not detectable by an assay based on antibody-antigen binding, the method comprising the steps of
exposing the biological fluid or extract to an oxidizing agent or to a DC electric current sufficient to alter a binding specificity of the autoantibody so that the autoantibody becomes capable of binding to an antigen, thereby becoming detectable and recoverable from the biological fluid or extract by an antibody-antigen binding, wherein said oxidizing agent is a compound that is capable of altering the redox state of a biological molecule by being reduced and acting as an electron acceptor for other molecules that act as electron donors, said oxidizing agent being at a concentration sufficient to alter the binding specificity of said autoantibody but less than a concentration that would destroy or denature said autoantibody, and
detecting the autoantibody in the biological fluid and/or isolating and recovering the autoantibody from the biological fluid by binding of the autoantibody to antigen.

28. The method of claim 27 wherein said biological fluid is from a vertebrate.

29. The method of claim 27 wherein said biological fluid is from a mammal or bird.

30. The method of claim 27 wherein said biological fluid is from a human.

31. The method of claim 27 wherein said biological fluid comprises diluted whole blood, diluted serum, diluted plasma, raw milk, lymphatic fluid, or CNS fluid.

32. The method of claim 27 wherein said biological fluid comprises diluted whole blood, serum, plasma, raw milk, lymphatic fluid, or CNS fluid that is pooled from a plurality of subjects.

33. The method of claim 27 wherein the composition comprises intravenous immunoglobulin (IvIg).

34. The method of claim 27 wherein autoantibody an IgG, IgA, or IgM isotype.

35. The method of claim 27 wherein the biological fluid is mammalian milk and the autoantibody is an IgA autoantibody.

36. The method of claim 27 wherein the biological fluid is CNS fluid and the autoantibody is an IgG autoantibody.

37. The method of claim 27 wherein the oxidizing agent is a ring compound containing a coordinated metal.

38. The method of claim 27 wherein the oxidizing agent is a ring compound containing a coordinated iron.

39. The method of claim 27 wherein the oxidizing agent is hemin.

40. The method of claim 27 wherein the oxidizing agent is $KMnO_4$.

41. The method of claim 27 wherein the oxidizing agent is chlorophyll.

42. The method of claim 27 wherein the autoantibody is selected from the group consisting of an antibody specific for glutamic acid decarboxylase (GAD);
an antibody specific for tyrosine phosphatase (IA-2);
an anti-lupus anticoagulant antibody;
an anti-phospholipid antibody;
an antinuclear antibody (ANA);
an anti-lamin antibody;
an anti-nucleolus antibody;
an anti-nuclear membrane antibody;
an anti-mitochondria antibody;
an anti-Golgi antibody;
an anti-granulocyte antibody;
an anti-neutrophil antibody;
an anti-monocyte antibody;
an anti-B lymphocyte antibody;
an anti-myeloperoxidase antibody;
an anti-islet cell antibody;
an anti-factor VIII antibody;
an anti-platelet factor 4/heparin complex antibody; and
an anti-beta2-glycoprotein I antibody.

43. The method of claim 27 wherein the masked protein is selected from the group consisting of anticardiolipin, antiphosphatidylcholine, antiphosphatidylethanolamine and antiphosphatidylserine.

44. The method of claim 10, wherein the antibody is a autoantibody.

45. The method of claim 21, wherein the antibody is a autoantibody.

* * * * *